US012268692B2

(12) United States Patent
Hahn

(10) Patent No.: US 12,268,692 B2
(45) Date of Patent: Apr. 8, 2025

(54) COMBINATORIAL TARGETED THERAPY METHODS

(71) Applicant: Postsurgical Therapeutics, Inc., Costa Mesa, CA (US)

(72) Inventor: Soonkap Hahn, Irvine, CA (US)

(*) Notice: Subject to any disclaimer, the term of this patent is extended or adjusted under 35 U.S.C. 154(b) by 0 days.

(21) Appl. No.: 18/406,053

(22) Filed: Jan. 5, 2024

(65) Prior Publication Data
US 2024/0207272 A1 Jun. 27, 2024

Related U.S. Application Data

(63) Continuation-in-part of application No. 17/227,992, filed on Apr. 12, 2021, now abandoned.

(60) Provisional application No. 63/008,554, filed on Apr. 10, 2020.

(51) Int. Cl.
| A61K 31/436 | (2006.01) |
| A61K 9/50 | (2006.01) |
| A61K 31/519 | (2006.01) |
| A61K 45/06 | (2006.01) |
| A61P 35/00 | (2006.01) |
| C12Q 1/6886 | (2018.01) |

(52) U.S. Cl.
CPC .......... *A61K 31/519* (2013.01); *A61K 9/5031* (2013.01); *A61K 31/436* (2013.01); *A61K 45/06* (2013.01); *A61P 35/00* (2018.01); *C12Q 1/6886* (2013.01); *C12Q 2600/106* (2013.01)

(58) Field of Classification Search
None
See application file for complete search history.

(56) References Cited

U.S. PATENT DOCUMENTS

| 7,378,423 B2 | 5/2008 | Kawasaki et al. | |
| 2004/0091929 A1 | 5/2004 | Galvin et al. | |
| 2015/0025106 A1* | 1/2015 | Kwon | A61K 31/436 514/183 |
| 2021/0315870 A1* | 10/2021 | Hahn | A61K 47/593 |

FOREIGN PATENT DOCUMENTS

| WO | 2003087306 A2 | 10/2003 |
| WO | 2004070062 A2 | 11/2004 |
| WO | 2007146959 A2 | 12/2007 |

OTHER PUBLICATIONS

Sicklick et al., Molecular profiling of cancer patients enables personalized combination therapy: the I-PREDICT study. Nature Medicine (2019), 25: 744-750 (Year: 2019).*
Pogrebniak et al., Harnessing Tumor Evolution to Circumvent Resistance. Trends in Genetics (2018), 34(8): 639-651 (Year: 2018).*
AFINITOR Highlights of Prescribing Information, published Jul. 2012 (Year: 2012).*
Houdaihed et al., Dual-Targeted Delivery of Nanoparticles Encapsulating Paclitaxel and Everolimus. Pharm Res (2020), 37:39, 1-10 (Year: 2020).*
Zheng et al. Co-delivery of sorafenib and metapristone encapsulated by CXCR4-targeted PLGA-PEG nanoparticles overcomes hepatocellular carcinoma resistance to sorafenib. Journal of Experimental & Clinical Cancer Research (2019) 38:232, 1-18 (Year: 2019).*
Liu et al., MEK inhibition overcomes everolimus resistance in gastric cancer. Cancer Chemotherapy and Pharmacology (2020) 85: 1079-1087 (Year: 2020).*
Patel et al., A Review on PLGA Based Solvent Induced In-situ Forming Implant. Inventi Rapid: NDDS vol. 2015, Issue 4, pp. 1-14 (Year: 2015).*
Sutter et al., Delivery of Rapamycin Using In Situ Forming Implants Promotes Immunoregulation and Vascularized Composite Allograft Survival. Scientific Reports (2019), 9:9269, pp. 1-16 (Year: 2019).*
"International Search Report," Patent Cooperation Treaty, Jul. 16, 2021.
Non-Final Office Action, issued by USPTO, Jul. 19, 2023.
Sicklick et al., Molecular profiling of cancer patients enables personalized combinatorial therapy: the I-PREDICT study. Nature Medicine (2019), 25:744-750 (Year: 2019).
Houdaihed et al., Dual-Targeted Delivery of Nanoparticles Encapsulating Paclitaxel and Everolimus: a Novel Strategy to Overcome Breast Cancer Receptor Heterogeneity. Pharm Res (2020), 37:39, 1-10 (Year: 2020).
Zheng et al. Co-delivery of sorafenib and metapristone encapsulated by CXCR4-targeted PLGA-PEG nanoparaticles overcomes hepatocellular carcinoma resistance to sorafenib. Journal of Experimental & Clinical Cancer Research (2019) 38:232, 1-18 (Year: 2019).
Extended European Search Report, mailed Apr. 19, 2024, issued by European Patent Office.

(Continued)

*Primary Examiner* — Celine X Qian
*Assistant Examiner* — Catherine Konopka
(74) *Attorney, Agent, or Firm* — CIONCA IP Law P.C.

(57) ABSTRACT

A combinatorial targeted therapy method for treating cancer, including metastatic cancer in a subject is provided, the method being designed to prevent unacceptable level of systemic toxicity in the subject and thus forced stoppage of the treatment, by performing initial molecular diagnostics to detect genomic alterations at each cancer site of the subject; for each cancer site, designing an initial combination targeted therapy by selecting a plurality of targeted drugs, based on the results of the initial molecular diagnostic at each cancer site; assigning each targeted drug to systemic or local delivery method, based on each targeted drug's properties; simultaneously treating all cancer sites according to the designed initial combination targeted therapy for each site, by delivering each targeted drug according to assigned delivery method to each targeted drug; and monitoring the progress of the cancer at each cancer site by performing follow-up molecular diagnostics at each cancer site.

11 Claims, 17 Drawing Sheets

(56) References Cited

OTHER PUBLICATIONS

Bissan Al-Lazikani, Banerji Udai, Workman Paul: "Combinatorial drug therapy for cancer in the post-genomic era", Nature Biotechnology, Nature Publishing Group US, New York, vol. 30, No. 7, Jan. 1, 2012 (Jan. 1, 2012), pp. 1-13, XP055370881, DOI: 10.1038/nbt. 2284.

Hidetoshi Hayashi et al: "Randomized Phase II Trial Comparing Site-Specific Treatment Based on Gene Expression Profiling With Carboplatin and Paclitaxel for Patients With Cancer of Unknown Primary Site", Journal of clinical oncology, Jan. 17, 2019 (Jan. 17, 2019), XP055693048, DOI: 10.1200/JC0.18, Retrieved from the Internet: URL:https://ascopubs.org/doi/pdfdirect/10.1200/JCO.18. 00771.

Chen Jeane et al: "Poly(lactide-co-glycolide) microspheres for MRI- monitored delivery of sorafenib in a rabbit VX2 model", Biomaterials, Elsevier, Amsterdam, NL, vol. 61, May 15, 2015 (May 15, 2015), pp. 299-306, XP029229967, ISSN: 0142-9612, DOI: 10.1016/J.BIOMATERIALS.2015.05.010.

Laborde Laurent et al: "Continuous low plasma concentrations of everolimus provides equivalent efficacy to oral daily dosing in mouse xenograft models of human cancer", Cancer Chemotherapy and Pharmacology, vol. 80, No. 4, Aug. 4, 2017 (Aug. 4, 2017), pp. 869-878, XP036325331, ISSN: 0344-5704, DOI: 10.1007/S00280-017-3407-5.

Ymera Pignochino et al: "The combination of sorafenib and everolimus shows antitumor activity in preclinical models of malignant pleural mesothelioma", BMC Cancer, Biomed Central, London, GB, vol. 15, No. 1, May 8, 2015 (May 8, 2015), p. 374, XP021221020, ISSN: 1471-2407, DOI: 10.1186/S12885-015-1363-1.

Pawaskar Dipti K et al: "Synergistic interactions between sorafenib and everolimus in pancreatic cancer xenografts in mice", Cancer Chemotherapy and Pharmacology, Springer Verlag, Berlin, DE, vol. 71, No. 5, Mar. 3, 2013 (Mar. 3, 2013), pp. 1231-1240, XP035339899, ISSN: 0344-5704, DOI: 10.1007/S00280-013-2117-X.

Al-Lazikani et al. "Combinatorial drug therapy for cancer in the post-genomic era." Jul. 2012 Nature Biotechnology. pp. 1-13, Table 1, abstract, p. 1, right col. para 2, Figure 5, p. 4, left col. para 2, p. 10, left col. para 3-4, p. 8, right col. para 4, p. 4, right col. para 1, p. 9, right col. para 3.

Rezvantalab et al. "PLGA-Based Nanoparticles in Cancer Treatment" Nov. 2, 2018 Frontiers in Pharmacology, pp. 1-19, abstract, p. 3, left col. para 1-2, p. 10, right col. para 4, p. 2, right col. para 1.

International Preliminary Report on Patentability, Patent Cooperation Treaty, issued Oct. 5, 2022.

* cited by examiner

C26 UNTREATED = Cell culture medium + C26 cells
DILUENT = 100 μL of diluent (0.5% CMC + 0.1% Tween20 + PBS buffer) + cell culture medium + C26 cells

COMBINATORIAL TARGETED THERAPY METHODS

CROSS-REFERENCE TO RELATED APPLICATIONS

This application is a continuation-in-part and claims the benefit of U.S. Non-Provisional application Ser. No. 17/227,992, filed Apr. 12, 2021, which claims the benefit of U.S. Provisional Application No. 63/008,554, filed Apr. 10, 2020, which are each hereby incorporated by reference, to the extent that they are not conflicting with the present application.

BACKGROUND OF INVENTION

1. Field of the Invention

The invention relates generally to methods of treating cancer and specifically to a combinatorial targeted therapy to treat cancer patients at early or metastatic stage and a method of reducing the systemic drug toxicity while controlling the resistance issue faced by the current targeted therapy.

2. Description of the Related Art

There were approximately 12.7 million new cases of cancer and 8 million people died in 2008 worldwide. This rate increased to 18.1 million new cases of cancer and 9.6 million deaths worldwide in 2018. This makes cancer the leading cause of death in the developed world and the second leading in the developing world. People with cancer have been increasing primarily due to longer lifespan and life style change in developing countries.

Cancer is a complex disease that results from uncontrolled division and growth of cells. The uncontrolled division and growth of cells are due to genomic alterations caused by environmental, lifestyle factors or inherited genetics. The environmental and lifestyle factors include pollution, tobacco use, obesity, infections and radiation.

Cancer is currently treated with various methods: 1) surgery, 2) chemotherapy, 3) targeted therapy and 4) radiation. Among them, both chemotherapy and targeted therapy are effective for treating cancer. However, chemotherapy can kill normal, healthy cells along with cancer cells thus causing some side effects. In contrast, targeted therapy (so called "precision medicine" or "personalized medicine") interferes with molecules specific to cancer cells and kills only cancer cells. Although this selectivity improves overall survival rates and reduces side effects, the cancer cells eventually develop resistance to the therapy in virtually every patient.

There are two types of resistance: 1) preexisting resistance and 2) acquired resistance during treatment. Both types of resistance may involve a number of complex mechanisms. If a certain targeted drug blocks one mechanism, the cancer cells can mutate and activate other mechanisms to grow.

To reduce the limitations associated with the above resistance issue, various methods have been attempted. One of the methods is to combine and administer several targeted drugs simultaneously. This method blocks potential pathways that cancer cells may escape to, if the initial pathway is blocked. However, according to these methods, the targeted drugs are taken orally or intravenously. That is a serious problem. That is because each targeted drug asserts some systemic toxicity, causing side effects. Further, the toxicities asserted by several targeted drugs accumulate and cause some very serious systemic side effects. This systemic toxicity issue prohibits this combination targeted therapy method from being used more frequently by cancer patients and often needs to be stopped because unacceptable systemic toxicity levels are reached.

In addition, if the primary cancer is spread to other organ(s) as secondary cancer (metastatic cancer), there is no currently reliable treatment option to cure or even slow down the progression of the cancer. That is because the primary cancer or secondary cancer may have its own multiple heterogeneous resistance mechanisms, and thus, adequately treating both primary and secondary cancer sites may require a different combination targeted therapy for each cancer site. Currently, due to cumulative systemic side effects via oral or intravenous (IV) delivery, it is not possible to use a different combination targeted therapy for each cancer site. For example, if a cancer patient has 5 (five) cancer sites, each site requiring 2 (two) distinct targeted drugs, the systemic administration via oral or intravenous (IV) delivery of the cumulative 10 (ten) targeted drugs are likely to cause an unacceptable level of systemic toxicity in the cancer patient. Using the currently known targeted therapies, 10-30% of patients cannot continue treatment due to the cumulative toxicity.

Therefore, there is a need to solve the serious shortcomings of current cancer therapies described hereinabove.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description.

In an aspect, the combinatorial targeted therapy method disclosed herein may include five or six principal steps:
1) Performing initial molecular diagnostics to detect genomic alterations at each cancer site of a subject;
2) Designing and selecting an initial combination targeted therapy for each cancer site, based on the results of the initial molecular diagnostics;
3) Assigning of each targeted drug to systemic or local delivery, based on each targeted drug's properties;
4) Simultaneously delivering the initial combination targeted drugs using suitable delivery device;
5) Monitoring the progress of cancer at each cancer site by performing follow-up molecular diagnostics;
6) And, preferably, maintaining the initial combination targeted therapy or designing a follow-up combination targeted therapy, based on the follow-up molecular diagnostics for each cancer site.

The combinatorial targeted therapy method disclosed herein has the advantage of being useful for treating both post- and pre-surgery cancer patients at early or even metastatic stages. Specifically, the disclosed method has the benefit of reducing the limitations faced by the current cancer treatment methods when they attempt to control the resistance to drugs developed by the cancer cells. Further, the combinatorial targeted therapy method disclosed herein allows for selective and simultaneous combined targeted therapy at multiple cancer sites through both systemic and local means, while controlling cumulative systemic toxicity, which is a major shortcoming of the current treatment methods, as indicated hereinabove.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

Figure 1:
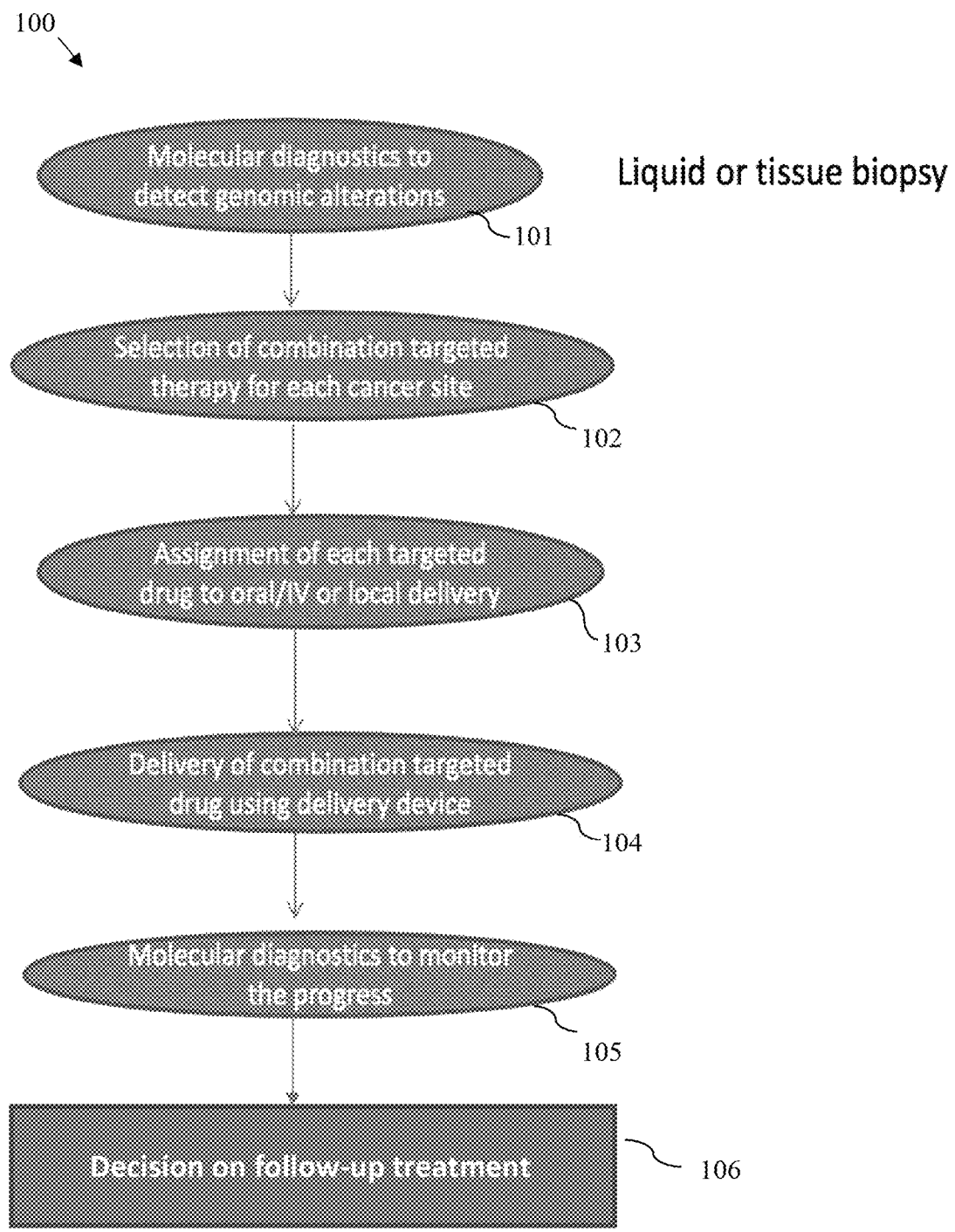
FIG. 1 illustrates a flowchart depicting the steps of the combinatorial targeted therapy method disclosed herein, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention.

It should be understood that, for clarity of the drawings and of the specification, some or all details about some structural components or steps that are known in the art are not shown or described if they are not necessary for the invention to be understood by one of ordinary skills in the art.

In order to address and solve the issues presented by current cancer therapies, the invention disclosed herein, in an aspect, teaches the use of local intratumoral injection (i.e., local delivery) along with oral or IV delivery to treat multiple cancer sites without causing serious systemic side effects, as it will be described in more detail hereinafter. The cumulative systemic side effects caused by oral or IV delivery can be reduced significantly by selectively delivering targeted drugs locally, which limits the systemic absorption of delivered targeted drugs, as it will be described in more detail hereinafter. The disclosed combinatorial targeted therapy addresses existing shortcomings of current therapies by maximizing efficacy, reducing the limitations associated with controlling cancer cells' resistance to targeted therapies and minimizing systemic side effects associated with existing targeted therapies.

The properties inherent to combinatorial targeted therapy provide this method with significant advantages over current therapies. The overall reduction of total targeted drugs delivered systemically reduces the associated systemic toxicity, allowing for a greater variety of targeted drugs to be delivered through local means. This advantage enables this process to counteract the limitations associated with the aforementioned resistance issues, while simultaneously minimizing the resulting toxicity. Due to the reduced systemic toxicity enabled by the disclosed method, i.e., the combinatorial targeted therapy, more options are provided for advanced stage cancer patients (metastatic cancer patients) as well as cancer patients with very little treatment options, such as pancreatic cancer patients.

FIG. 1 illustrates a flowchart depicting the steps of the combinatorial targeted therapy method disclosed herein, according to an aspect. As shown, in an aspect, the combinatorial targeted therapy method 100 disclosed herein includes six principal steps: performing initial molecular diagnostics to detect genomic alterations (step 101), designing and selecting an initial combination targeted therapy for each cancer site based on the initial molecular diagnostics (step 102), assigning of each targeted drug to systemic or local delivery, based on each targeted drug's properties (step 103), delivering the initial combination targeted drugs using suitable delivery device or method (step 104), monitoring the progress of cancer at each cancer site by performing follow-up molecular diagnostics (step 105) and, preferably, maintaining the initial combination targeted therapy or designing a follow-up combination targeted therapy based on the follow-up molecular diagnostics (step 106).

Molecular diagnostics using liquid biopsy (i.e., blood) or tissue biopsy sample can detect genomic alterations (step 101) specific to each cancer patient and also specific to each cancer site, if the patient has more than one cancer site. Based on the information of these genomic alterations, oncologists can design and select an initial combination targeted therapy specific to the patient and, if applicable to that patient, to each cancer site (step 102).

Once the combination targeted therapy is determined, each drug in the initial targeted therapy can be assigned to either systemic (oral/IV) or local delivery (step 103) depending on its property. One drug property would be for example the known systemic toxicity level caused by the drug, so that drugs with high systemic toxicity would be assigned to local delivery instead of systemic delivery. Further, it is needed to deliver some drug(s) with low potency by oral delivery daily (i.e., requiring more than 500 mg oral delivery daily to be effective for treating cancer). That is because if a drug has low potency, it would have to be delivered in a very large amount locally, for a sustained, controlled release over a long period (e.g., over 1-6 months). However, it is difficult to deliver the very large amount locally. Thus, the systemic delivery is generally the better option for low potency drugs. From the above considerations, three rules may be used to determine proper delivery method assignments; low potency drugs requiring more than 500 mg oral delivery daily are to be delivered systemically, high potency drugs requiring less than 500 mg oral delivery daily are to be delivered locally and drugs causing frequent grade 3 or 4 systemic toxicity are to be delivered locally.

In addition, other considerations may need to be taken into account when assigning the drug to either oral/IV (i.e., systemic) or local delivery (step 103). For example, some types of cancer are difficult to reach locally. In that case, systemic delivery may need to be considered. However, if the drug is highly potent (i.e., requiring less than 50 mg oral delivery daily), endoscopic image-guided injection method, for example endoscopic ultrasound image-guided fine needle injection method, can be used for delivering a small amount of drug into tumor tissue. This injection method is complex and not ideal for frequent delivery. In addition, it is not easy to deliver a large amount of drug using this method.

Thus, in an example, if, let's say, two targeted drugs are needed for one cancer site that is accessible, both drugs will preferably be delivered locally. If however, one of the drugs has low potency, that drug would be delivered systemically instead, by for example daily oral delivery. That is because, due to the typical high complexity of the local delivery procedure, local delivery may not routinely be used, e.g., daily.

In step 104, the targeted drug(s) are delivered using the suitable delivery device or method. Targeted drug encapsulated in biodegradable polymer such as polylactic glycolic acid (PLGA) can be delivered locally for sustained, controlled release over 1-6 months. For local delivery, if possible, tumor size or volume can be measured using imaging system such as ultrasound, MRI or other imaging system, before injection. The injected amount of targeted drug can be adjusted depending on the tumor size or volume. This adjustment is only possible through the implementation of local delivery and provides additional means of moderating system toxicity. This reliable means of drug adjustment is not possible with oral/IV delivery methods due to their indirect delivery method. Orally administered drugs must be absorbed through ingestion, and IV administered drugs must be carried through the bloodstream, which complicates drug dose adjustment determinations.

Targeted drug assigned for oral delivery can be taken as a tablet or capsule daily while that assigned for IV delivery is administered intravenously.

For local delivery, the delivery device can be for example a simple hand-held sprayer or image-guided delivery system. The simple hand-held sprayer is useful for treating post-surgery patients in the resected area after surgery. The image-guided delivery system is useful to deliver targeted drugs by intratumoral injection locally for pre-surgery patients. The image-guided delivery system has image-guided needle, syringe and imaging system. It can deliver targeted drugs in a powder form of microparticles or a solution form with suspended microparticles at multiple lesions. The imaging system includes ultrasound, CT, MRI and other imaging system.

After the combinatorial targeted therapy is administered, the progress of cancer is preferably monitored by follow-up molecular diagnostics (step 105). Depending on the results of the follow-up molecular diagnostics, the initial combinatorial targeted therapy can be maintained or modified (step 106).

Again, cancer is a complex disease caused by uncontrolled division and growth of cells. This abnormal division and growth of cells is due to genomic alterations. These genomic alterations are caused by various mechanisms which are variable from one cancer type to another one as well as from one person to another person. For example, breast cancer may be caused by different genomic alterations compared to lung cancer. Even for the same breast cancer, there are three different subtypes in HER-positive, estrogen receptor positive and triple negative subtype.

Chemotherapy generally treats breast cancer patient with one of carboplatin, docetaxel, doxorubicin and paclitaxel by IV infusion regardless of their subtype. These drugs kill cancer cells as well as normal healthy cells causing side effects. In contrast, targeted therapy treats three subtypes of breast cancer patients differently based on their genomic alterations. For example, HER-2 positive patients have overexpressed HER-2 proteins. They are treated with lapatinib or trastuzumab which inhibits specifically the tyrosine kinase activity of HER-2. Since lapatinib and trastuzumab interfere only with HER-2, they are not effective for treating other subtype patients, estrogen receptor positive or triple negative patients. For estrogen receptor positive patients, a different combination targeted therapy of palbociclib and an aromatase inhibitor or fulvestrant can be used. Overall, this targeted therapy is more effective with less side effects compared to the above chemotherapy.

Another successful example is treating lung cancer with targeted therapy. About 85% of lung cancer is non-small cell lung cancer (NSCLC) subtype. The NSCLC patients can have multiple single nucleotide polymorphisms (SNPs) in epidermal growth factor receptor (EGFR). Patients with one or more of these mutations in EGFR respond well to EGFR tyrosine kinase inhibitors such as gefitinib and erlotinib, which block EGFR signaling. In patients without these mutations, EGFR is likely to function normally, so these drugs are unlikely effective. A similar approach can be taken for translocations in the ALK gene. Patients with ALK translocations respond well to treatment with crizotinib, a tyrosine kinase inhibitor which blocks the transmission of growth signals to the cell nucleus. As shown in these examples, the targeted therapy is more selective in treating cancer patients and has improved the overall survival rate significantly. With combinatorial targeted therapy, the use of these combination targeted therapies may be optimized to maximize efficacy, reduce the limitations associated with controlling cancer cells' resistance to targeted drugs and minimize systemic side effects. Through these optimizations, this method has the potential to provide more treatment options for both early and metastatic cancer patients.

Molecular diagnostics (step 101) is an essential method to detect genomic alterations. To detect genomic alterations, blood or tissue samples can be analyzed by various methods including next generation sequencing (NGS), fluorescence in situ hybridization (FISH) and other methods. Blood sample (liquid biopsy) has inherent advantage over tissue sample in terms of less invasiveness to collect and possibility of repeated samplings. Blood sample contains ct (circulating tumor) DNAs and circulating tumor cells (CTCs) shed from cancer cells into the blood stream. These are valuable to provide the information related to genomic alterations of each patient.

Once the genomic alterations are detected, oncologists can determine a matching targeted drug (step 102). For example, crizotinib is a right choice of targeted drug for a NSCLC patient with ALK translocations. A monotherapy of crizotinib is therapeutically effective initially for this patient. However, the patient eventually develops resistance to crizotinib by a mutation in ALK gene. By adding lorlatinib to crizotinib, the issues developed by the cancer cell's resistance are controlled and the patient can respond well. However, as stated hereinbefore, according to current methods, targeted drugs are taken either orally or intravenously. Again, this route of delivery has significant limitations on how many targeted drugs can be taken due to cumulative systemic side effects. Local delivery can reduce the systemic absorption of delivered targeted drugs significantly while maintaining their local level high.

The combinatorial targeted therapy method disclosed herein may also use oral/IV delivery as a systemic delivery method, along with local delivery. Again, as stated hereinbefore, in case a targeted drug has a low potency, it should be delivered orally. This dual mode of delivery may provide patients more treatment options and thus a higher likelihood of successful treatment of the cancer patients. The combinatorial targeted therapy method disclosed herein which combines oral/IV delivery with local delivery may provide a viable option to overcome the limitations associated with the developed resistances of cancer cells to targeted drugs and systemic toxicity issues described hereinbefore.

Again, as stated hereinbefore, currently, if the primary cancer is spread to other organ(s) as secondary cancer (metastatic cancer), there is no reliable treatment option to cure or even slow down the progression of the cancer. The primary cancer or secondary cancer may have its own multiple heterogeneous resistance mechanisms. Adequately treating both primary and secondary cancer sites may require a different combination targeted therapy for each cancer site. Currently, due to cumulative systemic side effects via oral or IV delivery, it is not possible to use current targeted therapy methods for each cancer site. The combinatorial targeted therapy method disclosed herein utilizes local intratumoral injection (i.e., local delivery) along with oral/IV administration to treat multiple cancer sites without causing serious systemic side effects. Local delivery of targeted drugs limits their systemic exposure while asserting their therapeutic effects to local cancer cells. Combining both local and oral/IV delivery may provide viable treatment option for both cancer patients at early stage and metastatic stage.

Once combination targeted therapy is determined (step 102), the oncologist needs to determine the route of delivery for each targeted drug, either oral/IV or local delivery. In this step, the most important parameter to consider is to maintain overall systemic toxicity below toxic level while maximizing efficacy. The three rules to apply in determining the delivery route are as follows; low potency drugs requiring more than 500 mg dose oral daily are delivered through oral/IV, high potency drugs requiring less than 500 mg dose oral daily are delivered through local means, and drugs causing frequent grade 3 or 4 systemic toxicity are delivered through local means.

The combinatorial targeted therapy method disclosed herein can be used by both post-surgery and pre-surgery cancer patients. When cancer is at an early stage (stage 1 or 2), the best treatment option is to remove tumor by surgery. Combinatorial targeted therapy can be used for prophylactic purpose to avoid the recurrence of cancer. In this case, combination targeted drugs encapsulated in PLGA microparticles can be sprayed by a simple hand-held sprayer. In addition, the combinatorial targeted therapy method disclosed herein may provide a viable treatment option for metastatic cancer patients. In this case, oncologist may design a combinatorial targeted drug regimen specific to each cancer site (i.e., primary cancer site as well as secondary cancer site(s)).

For local delivery, if possible, tumor size or volume can be measured using imaging system such as ultrasound, MRI or other imaging system before injection. The injection amount of targeted drug can be adjusted depending on the tumor size or volume. This adjustment capability is exclusive to local delivery methods, due to additional factors that may arise from systemic delivery methods that require the targeted drug to travel greater distances through the body before reaching the appropriate cancer site.

For local delivery, the combinatorial targeted therapy method disclosed herein uses an image-guided delivery system to deliver combination targeted drugs. Such a delivery system has an image-guided needle, syringe and imaging system. However, if a tumor is close to the skin or subcutaneous lesion or even palpable, the imaging system may not be needed. In case tumor lesion is not easily accessible, some additional instrument such as endoscopy may be needed to guide the needle. This delivery device can be linked with an imaging system such as ultrasound, MRI, CT or other imaging system. It can deliver combination targeted drugs as a powder or powder suspended in a solution at multiple lesions.

Each targeted drug can be encapsulated in a biodegradable polymer such as PLGA for sustained, controlled release over 1-6 months.

Targeted Drug Candidates

Targeted drugs block the growth and spread of cancer cells. Many targeted drugs have been approved by the FDA and others are currently being developed. The combinatorial targeted therapy method disclosed herein can use any of these drugs to design its combination targeted therapy. These targeted drugs include hormone therapies, signal transduction inhibitors, gene expression modulators, apoptosis inducers, angiogenesis inhibitors, immunotherapies, and toxin delivery molecules. The targeted drugs approved by the FDA are listed by cancer type in the following section:

Bladder cancer: atezolizumab, nivolumab, durvalumab, avelumab, pembrolizumab, erdafitinib Brain cancer: bevacizumab, everolimus Breast cancer: everolimus, tamoxifen, toremifene, trastuzumab, fulvestrant, anastrozole, exemestane, lapatinib, letrozole, pertuzumab, ado-trastuzumab emtansine, palbociclib, ribociclib, neratinib maleate, abemaciclib, olaparib, talazoparib tosylate, atezolizumab, alpelisib, fam-trastuzumab deruxtecan-nxki Cervical cancer: bevacizumab, pembrolizumab Colorectal cancer: cetuximab, panitumumab, bevacizumab, ziv-aflibercept, regorafenib, ramucirumab, nivolumab, ipilimumab Dermatofibrosarcoma protuberans: Imatinib mesylate Endocrine/neuroendocrine tumors: lanreotide acetate, avelumab, lutetium Lu 177-dotatate, iobenguane I 131

Endometrial cancer: pembrolizumab, lenvatinib mesylate

Esophageal cancer: trastuzumab, ramucirumab, pembrolizumab

Head and neck cancer: cetuximab, pembrolizumab, nivolumab

Gastrointestinal stromal tumor: imatinib mesylate, sunitinib, regorafenib

Giant cell tumor of the bone: denosumab

Kidney cancer: bevacizumab, sorafenib, sunitinib, pazopanib, temsirolimus, everolimus, axitinib, nivolumab, cabozantinib, lenvatinib mesylate, ipilimumab, pembrolizumab, avelumab Liver cancer: sorafenib, regorafenib, nivolumab, lenvatinib mesylate, pembrolizumab, cabozantinib, ramuciruma Lung cancer: bevacizumab, crizotinib, erlotinib, gefitinib, afatinib dimaleate, ceritinib, ramucirumab, nivolumab, pembrolizumab, osimertinib, necitumumab, alectinib, atezolizumab, brigatinib, trametinib, dabrafenib, durvalumab, dacomitinib, lorlatinib, entrectinib Lymphoma: Ibritumomab tiuxetan, denileukin diftitox, brentuximab vedotin, rituximab, vorinostat, romidepsin, bexarotene, bortezomib, pralatrexate, ibrutinib, siltuximab, idelalisib, belinostat, obinutuzumab, nivolumab, pembrolizumab, rituximab and hyaluronidase human, copanlisib hydrochloride, axicabtagene ciloleucel, acalabrutinib, tisagenlecleucel, venetoclax, mogamulizumab-kpkc, duvelisib, polatuzumab vedotin-piiq, zanubrutinib Microsatellite instability-high or mismatch repair-deficient solid tumors: pembrolizumab Multiple myeloma: bortezomib, carfilzomib, panobinostat, daratumumab, ixazomib citrate, elotuzumab, selinexor Myelodysplastic/myeloproliferative disorders: imatinib mesylate, ruxolitinib phosphate, fedratinib hydrochloride Neuroblastoma: dinutuximab Ovarian epithelial/fallopian tube/primary peritoneal cancers: bevacizumab, olaparib, rucaparib camsylate, niraparib tosylate monohydrate Pancreatic cancer: erlotinib, everolimus, sunitinib, olaparib Prostate cancer: cabazitaxel, enzalutamide, abiraterone acetate, radium 223 dichloride, apalutamide, darolutamide Skin cancer: vismodegib, sonidegib, ipilimumab, vemurafenib, trametinib, dabrafenib, pembrolizumab, nivolumab, cobimetinib, alitretinoin, avelumab, encorafenib, binimetinib, cemiplimab-rwlc Soft tissue sarcoma: pazopanib, alitretinoin Solid tumors with an NTRK gene fusion: larotrectinib sulfate, entrectinib Stomach (gastric) cancer: pembrolizumab, trastuzumab, ramucirumab Systemic mastocytosis: imatinib mesylate, midostaurin Thyroid cancer: cabozantinib, vandetanib, sorafenib, lenvatinib mesylate, trametinib, dabrafenib The drugs described above are either small molecules or antibodies. These molecules and targeted drugs developed in the future can be encapsulated in PLGA microparticles or in situ gelling (ISG) PLGA as a combination targeted therapy in the combinatorial targeted therapy method disclosed herein. If necessary, chemotherapy drugs can be also added into the combination therapy.

PLGA Microparticles

As described previously, the above targeted drugs include hormone therapies, signal transduction inhibitors, gene expression modulators, apoptosis inducers, angiogenesis inhibitors, immunotherapies, and toxin delivery molecules. Each drug group treats cancer caused by different genomic alterations. In addition, each drug group has its own subgroups. For example, signal transduction is associated with cell cycle progression and cell growth and related to 10 oncogenic signaling pathways. These 10 oncogenic signaling pathways are receptor tyrosine kinase/MAPK pathway, PI3K pathway, NRF2 pathway, TGFβ pathway, WNT pathway, MYC pathway, TP53 pathway, cell cycle pathway, HIPPO pathway and Notch pathway. Again each pathway has many proteins involved in various cell-related mechanisms. The disclosed method combines targeted drugs which block or inhibit two or more proteins from two or more groups, two or more subgroups, or two or more pathways for treating various cancer types. As an example, the present invention can combine inhibitors of receptor tyrosine kinase/MAPK pathway and PI3K pathway for treating various cancer types. Genomic alterations of these two pathways are associated with more than 60% of cancer patients.

PLGA is a biodegradable polymer with an excellent safety profile. A number of products with a drug encapsulated in PLGA are already approved by FDA. PLGA is a copolymer of lactic acid and glycolic acid. PLGA and a drug can be fabricated into microparticles including microcapsules and microspheres. Microcapsules generally have a drug core coated with a polymer film and may be spherical or non-spherical in shape. In contrast, microspheres have drugs dispersed evenly in polymer and are spherical in shape.

PLGA microparticles are a valuable drug delivery system due to their versatility in controlling drug release rate. The drug release rate from PLGA microparticle can be controlled by adjusting a number of parameters such as 1) ratio between polylactic acid (PLA) and polyglycolic acid (PGA), 2) molecular weight and 3) size of micro-particle.

In PLGA, polylactic acid is more hydrophobic compared to polyglycolic acid and subsequently hydrolyzes (i.e., degrades) slower. For example, PLGA 50:50 (PLA:PGA) exhibits a faster degradation than PLGA 75:25 due to preferential degradation of glycolic acid proportion if two polymers have the same molecular weights. PLGA with higher molecular weight exhibits a slower degradation rate than PLGA with lower molecular weight. Molecular weight has a direct relationship with the polymer chain size. Higher molecular weight PLGA has longer polymer chain and requires more time to degrade than lower molecular weight PLGA. In addition, an increase in molecular weight decreases drug diffusion rate and therefore drug release rate.

The size of a micro-particle also affects the rate of drug release. As the size of a micro-particle decreases, the ratio of surface area to volume of the micro-particle increases. Thus, for a given rate of drug diffusion, the rate of drug release from the micro-particle will increase with decreasing micro-particle size. In addition, water penetration into smaller micro-particle may be quicker due to the shorter distance from the surface to the center of the micro-particle.

In addition, the property and amount of drug can also affect the rate of drug release.

In an example, the drug powder disclosed herein uses microparticles having sizes between 1 μm and 250 μm, preferably less than 50 μm. The composition of PLGA preferably includes a ratio equal to or more than 50% by weight of polylactic acid (PLA). In one preferred embodiment, each PLGA micro-particle contains 1-50% of drug by weight. Molecular weight of PLGA may be between 7,000 and 150,000 Daltons, preferably 30,000 to 150,000 Daltons.

PLGA Microparticle Fabrication

Microparticles in the combinatorial targeted therapy method disclosed herein can be prepared by microencapsulation, spray drying, precipitation, hot melt microencapsulation, co-extrusion, precision particle fabrication (PPF) or other fabrication techniques. Microencapsulation techniques may use single, double or multiple emulsion process in combination with solvent removal step such as evaporation, extraction or coacervation step. They are the most commonly used techniques to prepare micro-particles. The above techniques including the microencapsulation techniques can be used for water soluble drug, organic solvent soluble drug and solid powder drug. The combinatorial targeted therapy method disclosed herein may also use hydrogel overcoating onto the surface of PLGA microparticles to extend the duration of drug release.

ISG PLGA

ISG PLGA formulation is a solution consisting of biocompatible organic solvent N-methyl-2-pyrrolidone (NMP), drug and PLGA (so called "atrigel"). Upon injection into the body, it becomes a solid gel. During the gelling process, it encapsulates the drug into the PLGA gel. Generally it is simpler to prepare and produce at large scale than PLGA microparticle. In addition, our ISG PLGA contains about 30-40% ethanol in NMP. Ethanol itself causes necrosis of cancer cells.

Hydrogel

Hydrogel is a hydrophilic polymer that can swell in water and hold a large amount of water. A three-dimensional structure results from the hydrophilic polymer chains held by crosslinks. The hydrogel is a very good absorbent which can absorb a large amount of water up to more than 10 times its own weight. It is used for many applications such as scaffolds in tissue engineering, sustained drug delivery system, breast implant, wound dressing, disposable diaper and other applications. The hydrogel can be prepared from synthetic polymer or natural polymer. The synthetic polymer includes polyhydroxyethyl methacrylate (PHEMA), polyethylene glycol (PEG), polyvinyl alcohol (PVA), polyvinylpyrrolidone (PVP), polyimide (PI), polyacrylate (PA), polyurethane (PU) and other synthetic polymers. The natural polymer includes collagen, hyaluronic acid, alginate, chitosan and other natural polymers.

Again, in one embodiment, the combinatorial targeted therapy method disclosed herein uses hyaluronic acid (HA) as its hydrogel component. It is a linear polysaccharide formed from N-acetyl-D-glucosamine and glucuronic acid with a molecular weight ranging from $2 \times 10^5$ to $1 \times 10^7$ daltons. It is naturally abundant in biological fluids and tissues. It is biocompatible, biodegradable, non-immunogenic and non-toxic. HA is used in many clinical applications such as intra-articular injection for treating osteoarthritis patients, wound healing, treating dry eye and other applications. Again, in an example, the drug powder is made by overcoating PLGA-drug microparticles with hyaluronic acid.

The HA-overcoated PLGA drug microparticles disclosed herein have many advantages over non-coated PLGA-drug microparticles. Some of these advantages are improved immunogenicity, potential zero-order drug release and longer drug release time.

Thus, the combinatorial aspects of the targeted treatment method disclosed herein include selecting and combining several drugs for specific targeting at each cancer site, selecting the appropriate delivery method for each individual drug, and simultaneously delivering each targeted drug to its proper cancer site and through its appropriate delivery mechanism.

Combinatorial targeted therapy provides solutions to the limitations faced by current cancer therapies in order to maximize efficacy, reduce the limitations associated with controlling the resistances of cancer cells to targeted drugs and minimize systemic side effects. The application of the aforementioned rules allows for the proper selection of delivery methods for each targeted therapy at each cancer site. Due to the advantages inherent to local delivery methods, monitoring of tumor size or volume may be followed up with proper adjustments to dosages, further optimizing efficacy and minimizing toxicity. Through the advances brought forth by combinatorial targeted therapy, additional treatments may become available to cancer patients with few treatment options, including advanced stage cancer (metastatic cancer) and pancreatic cancer patients. By overcoming the limitations that exist for current cancer therapies, combinatorial targeted therapy can provide life-saving treatment for those who would otherwise be untreatable.

Also provided herein are combinatorial targeted therapies relating to the KRAS (Kirsten Rat Sarcoma) viral oncogene. The KRAS viral oncogene is the most frequently mutated oncogene and is mutated in more than 20% of all solid tumors including lung cancer, colorectal cancer, pancreatic cancer and gastric cancer. The KRAS gene is a gene that encodes instructions for producing a protein called KRAS. This gene is involved in cell signaling and plays a crucial role in regulating cell growth and division. It belongs to MAPK (mitogen-activated protein kinase) pathway. Development of a drug which can block mutated KRAS has been an important therapeutic target but has also been a huge challenge due to its high affinity for guanine nucleotides and an apparent lack of readily discernable binding pockets for small molecule chemical inhibitors. However even if a drug is able to block the mutated KRAS path, cancer cells can respond by activating the alternate PI3K (phosphoinositide 3-kinase) pathway to resume growth. Therefore, the strategy of blocking both pathways by a combination of PI3K pathway inhibitor and MAPK pathway inhibitor has been pursued actively in clinical trials by many institutions. However, these clinical trials have used mainly systemic administration, either orally or intravenously, which has been found to cause serious cumulative systemic side effects. The inventor recognizing the shortcoming related to systemic administration has developed and applied a combinatorial targeted therapy method which utilizing local intratumor (IT) injection in order to overcome observed systemic toxicity.

EXAMPLES

As mentioned previously, treating cancer with a single targeted drug works initially. However, cancer cells develop resistance to this single targeted drug over time and cancer grows again. In order to reduce the issues that arise from these cancer cells' resistance to the targeted drug, another targeted drug(s) can be added to make a combination targeted therapy. As an example of the combination targeted therapy, sorafenib (MAPK pathway and RAF inhibitor) encapsulated in PLGA and everolimus (PI3K pathway and mTOR inhibitor) encapsulated in PLGA were combined and tested using a mouse model.

Preparation of Sorafenib-PLGA Microspheres

PLGA (1 g) was dissolved in 9.5 mL of dichloromethane (DCM) by stirring at room temperature (RT) for 1 hour (h). To the polymer solution, sorafenib (SOF: 200 mg) dissolved in 0.5 mL of dimethyl sulfoxide (DMSO) was added and stirred for an additional 10 minutes (min). The solution (oil phase) was poured into the dispersion phase tank of SPG membrane machine manufactured by MCTech and pressed through ceramic membrane with a pore size of 20 μm or 30 μm using nitrogen gas into the continuous phase tank filled with 4% polyvinyl alcohol (PVA) solution. This process is being carried out for about 2 h. The aqueous phase was transferred into a glass beaker and stirred with propeller stirrer for 4 h at RT to remove DCM. Then, cold deionized water (DI, 500 mL) was added to the microsphere solution and filtered on 20 μm filter paper or centrifuged at 3,000 rpm for 5 min after cooling down for 6 h at 4° C., followed by washing with cold water (1 L). The collected pellets were freeze-dried for 24-48 h and vacuum dried for 72-96 h at 39° C. in vacuum oven.

Preparation of Everolimus-PLGA Microspheres

PLGA (1 g) was dissolved in 9 mL of dichloromethane (DCM) by stirring at room temperature (RT) for 1 h. To the polymer solution, everolimus (EVE: 100 mg) was added and stirred for additional 10 minutes. The solution (oil phase) was poured into the dispersion phase tank of SPG membrane machine manufactured by MCTech and pressed through ceramic membrane (a pore size of 30 μm) using nitrogen gas into the continuous phase tank filled with 4% PVA solution. Then, the same process described in the above example was followed.

In Vitro Release Study of Sorafenib and Everolimus

The in vitro release study was carried out by sample-and-separate method. Briefly, 5 mg of microsphere sample (n=3) was taken into 100 mL flask and dispersed in 50 mL of release medium (0.5% Tween 20 and 0.1% sodium azide in phosphate-buffered saline (PBS at pH 7.4)). The flasks were placed in orbital agitating incubator at 37° C. and shacked at 100 rpm. At certain time points, 40 mL medium was taken and centrifuged at 3000 rpm for 2 min. From the supernatant, 30 mL was pipetted and replaced by same amount of the fresh media. In the collected supernatant, the content of the released SOF or EVE was analyzed by high performance liquid chromatography (HPLC). Since EVE was known to degrade quickly in aqueous solution as free form, we decided to analyze EVE content in the microsphere residue. We confirmed that EVE was stable inside the microsphere.

Figure 2A:
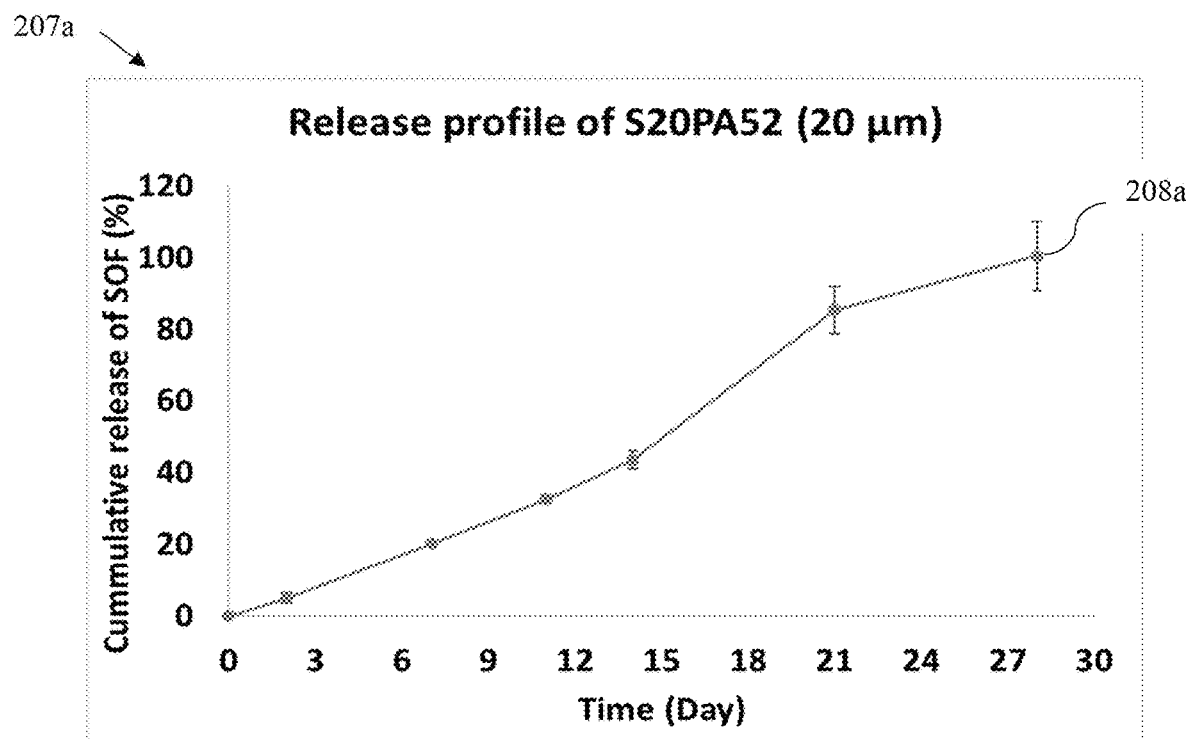
FIG. 2A is a graph showing the in vitro release profile of sorafenib encapsulated in S20PA52 PLGA polymer.
Figure 2B:
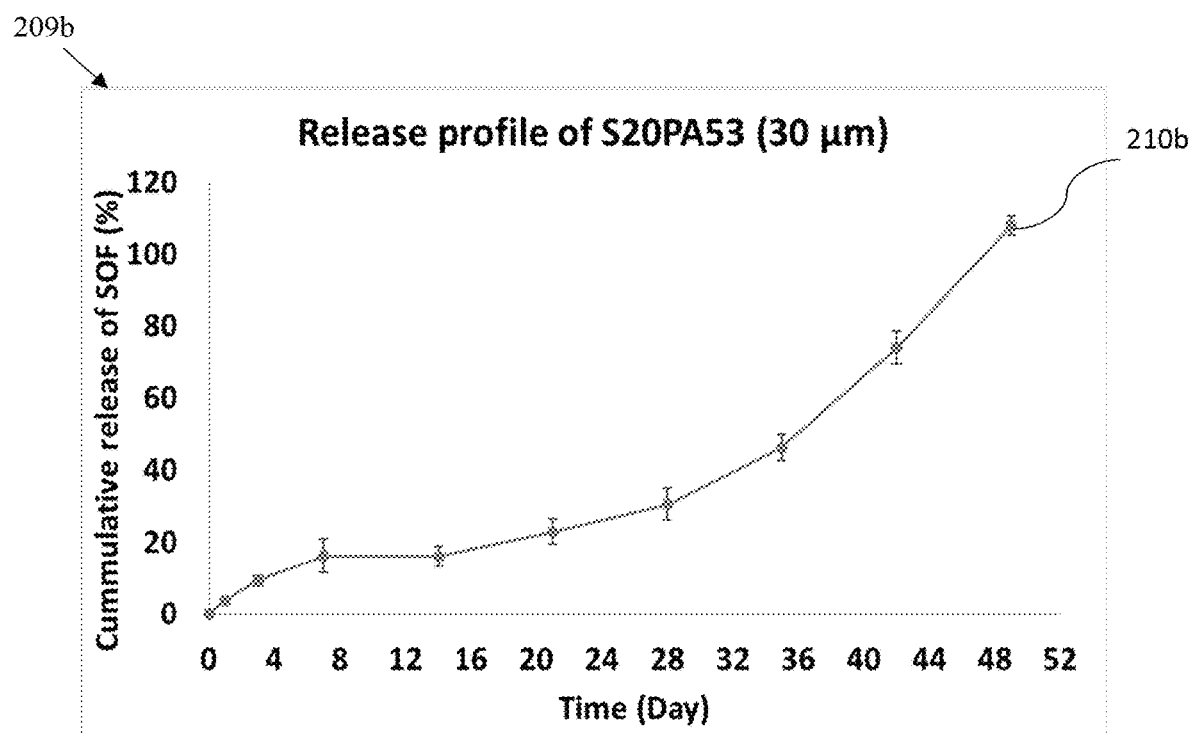
FIG. 2B is a graph showing the in vitro release profile of sorafenib encapsulated in S20PA53 PLGA polymer.

Sorafenib was encapsulated in two different PLGA polymers with acid terminated PLGA with molecular weight (MW) of 20,000 daltons and a ratio of PLA:PGA=50:50 (S20PA52) (207a) and MW of 30,000 daltons and a ratio of PLA:PGA=50:50 (S20PA53) (209b). S20PA52 was prepared using a membrane with a pore size of 20 μm which produced a mean size of 30 μm microspheres while S20PA53 with a pore size of 30 μm which produced a mean size of 47 μm microspheres. The in vitro sorafenib release profiles of these two microspheres are described in FIGS. 2A and 2B, respectively. S20PA53 with larger MW PLGA and larger size of microspheres (100% release in about 47 days) (210b) releases sorafenib much slower than S20PA52 (100% release in about 30 days) (208a).

Figure 3:
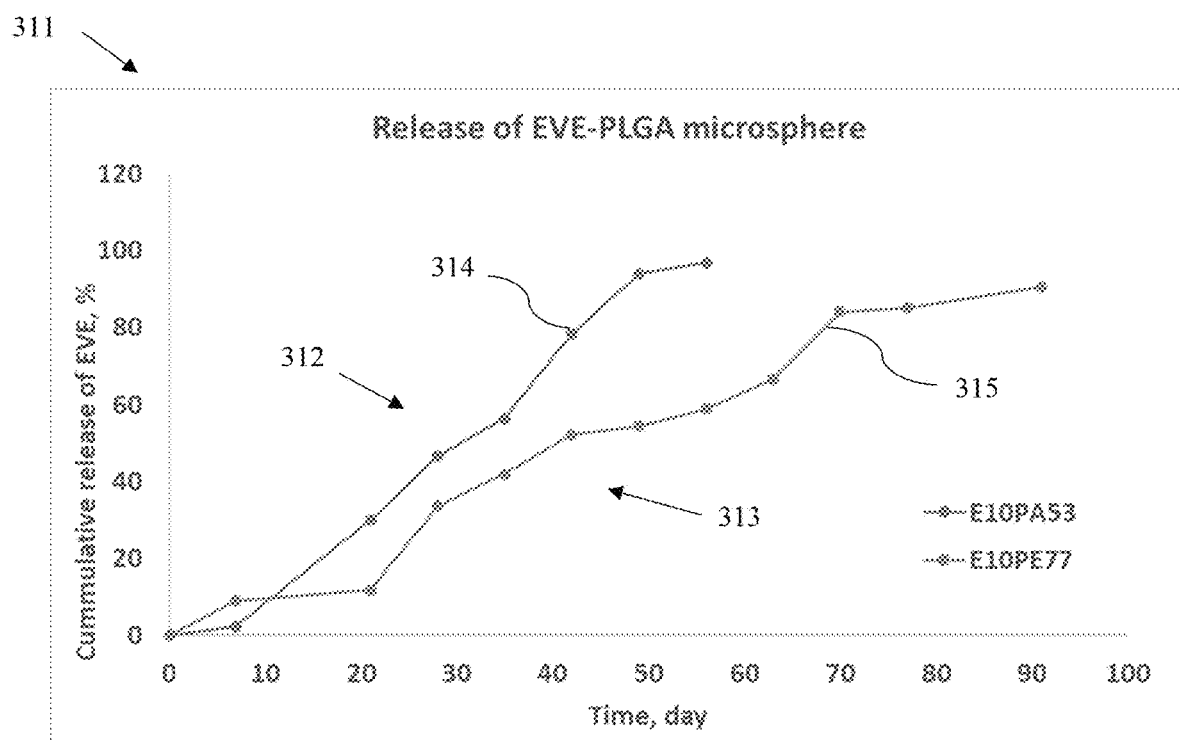
FIG. 3 is a graph showing the in vitro release profiles of everolimus encapsulated in two different PLGA polymers, E10PA53 and E10PE77.

Everolimus was also encapsulated in two different PLGA polymers (311) (acid terminated PLGA with MW of 30,000 daltons and a ratio of PLA:PGA=50:50 (E10PA53) (312) and ester terminated PLGA with MW of 70,000 daltons and a ratio of PLA:PGA=75:25 (E10PE77) (313). The in vitro everolimus release profiles of these two microspheres are described in FIG. 3. E10PE77 with larger MW and higher ratio of PLA:PGA (80% release in 70 days) (315) releases everolimus much slower than E10PA53 (80% release in 40 days) (314).

Multi-Side Hole Needles

A unique needle configuration is also provided as an example. Instead of having a hole at the tip of needle, the provided needle has multi-side holes. This configuration will aid injected drug formulation to disperse well throughout whole tumor tissue. This multi-side hole needle has been known. However, the needles provided herein have a unique configuration. The size of the holes near the syringe is smaller than that of those near the tip of needle. This configuration will distribute the injected drug more evenly throughout the whole tumor tissue.

The above demonstrates that it is possible to encapsulate both sorafenib and everolimus in PLGA polymers, and thus control their release at the cancer site, which is needed when administering them via local delivery, according to the combinatorial targeted cancer treatment method disclosed herein.

KRAS Viral Oncogene Combinatorial Targeted Therapies

In order to demonstrate the usefulness of the methods described above when referring to the KRAS viral oncogene, the following developed and tested combination targeted therapies are provided herein:

Combination-1=sorafenib (RAF inhibitor) and everolimus (mTOR inhibitor)

Combination-2=trametinib (MEK inhibitor) and everolimus

Figure 4:
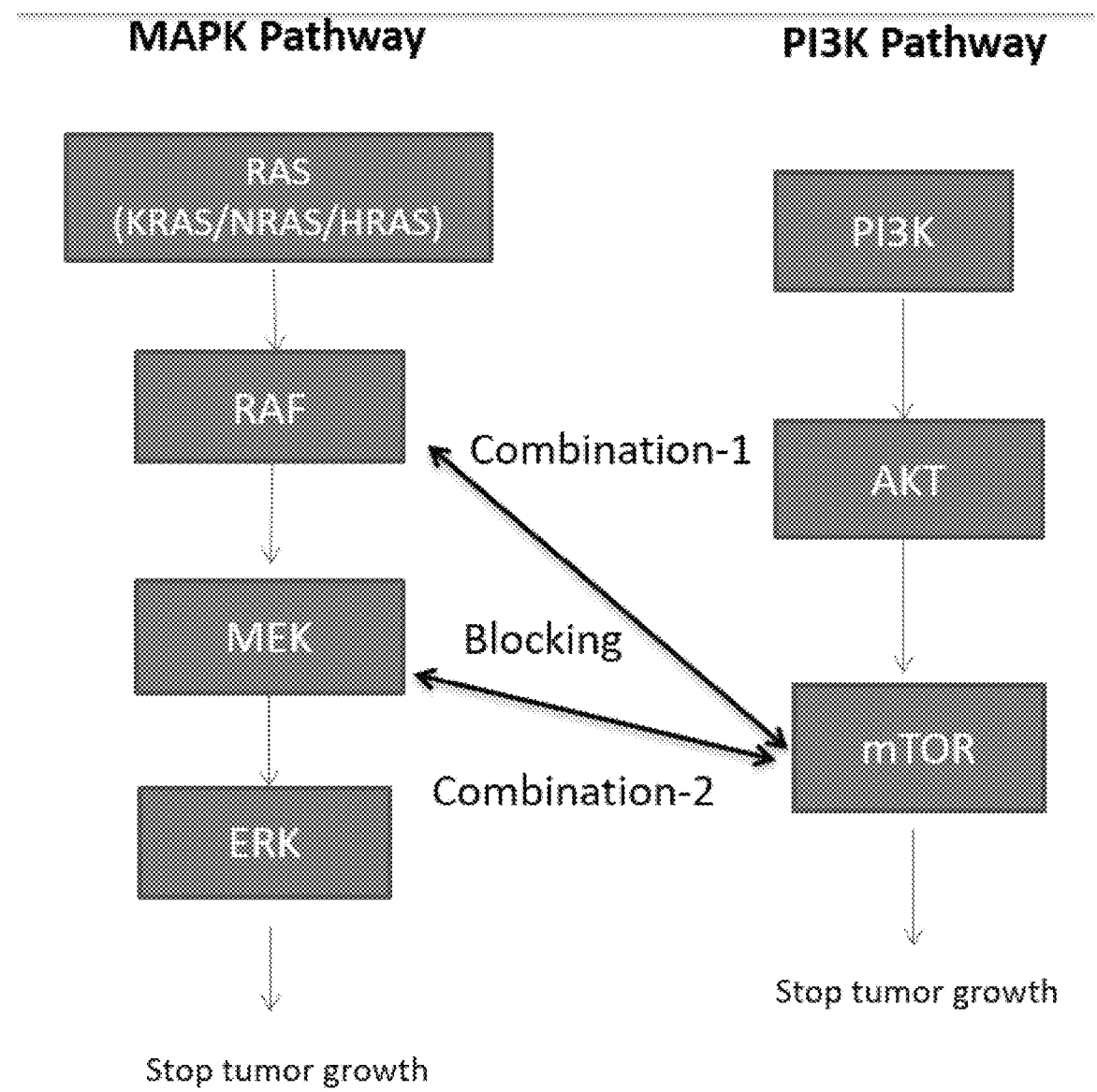
FIG. 4 is a diagrammatic flow chart depicting blockage of RAF or MEK and mTOR in the MAPK and PI3K pathways by the combination therapies provided herein.

The rationale for developing the above two combinations is described as follows. The MAPK pathway consists of four family proteins known as RAS, RAF, MEK and ERK while PI3K pathway consists of three family proteins known as PI3K, AKT and mTOR (shown in FIG. 4). Within the MAPK pathway, KRAS is one of three genes within the RAS family with two other genes known as HRAS and NRAS. Theoretically, any inhibitors related to these two pathways (i.e. one family protein from MAPK pathway and another family protein from PI3K pathway) could be used to block both pathways. Instead of inhibiting mutated KRAS directly, the inventor has opted to block downstream proteins. The inventor designed combination-1 to block RAF and mTOR and combination-2 to block MEK and mTOR to demonstrate proof-of-principle (shown in FIG. 4). Details pertaining to the development and testing of these two combinations are described in the following sections.

In Vitro and In Vivo Study for Combination-1

In Vitro Study

Figure 5:
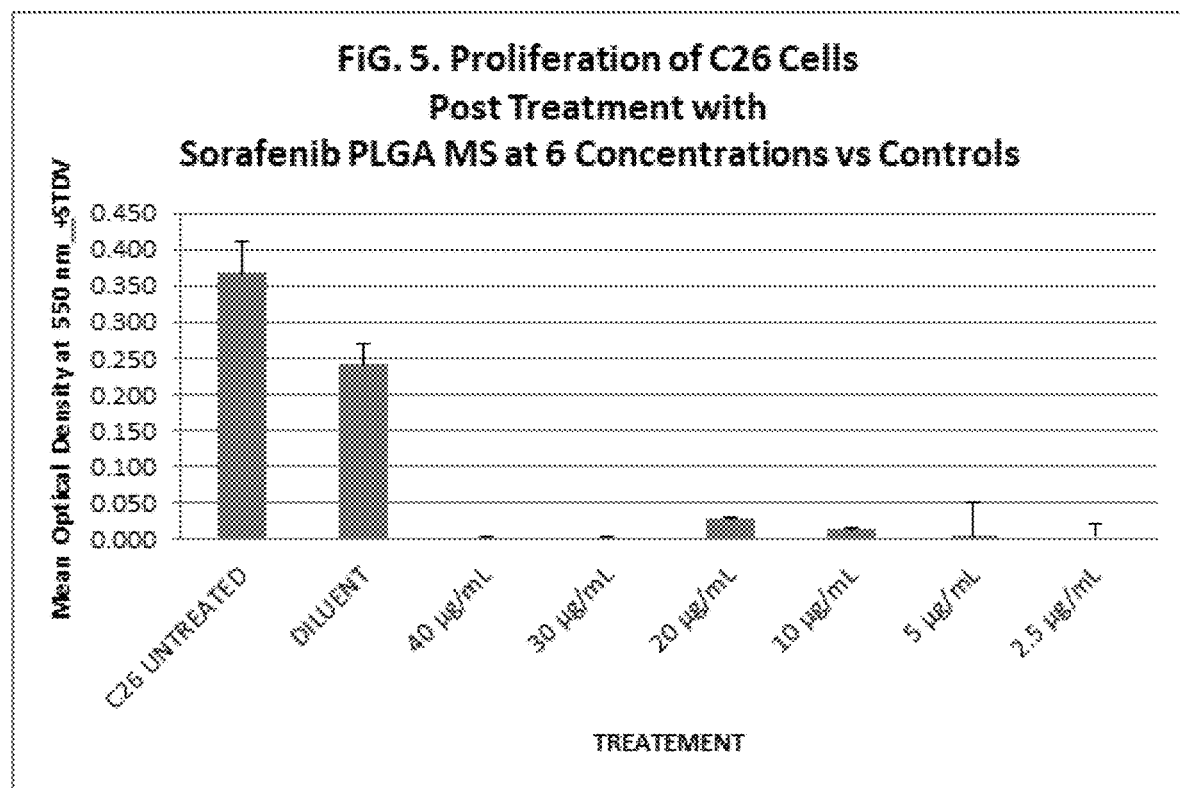
FIG. 5 summarizes the results of an in vitro study using C26 cells treated with sorafenib-PLGA microspheres, showing the proliferation of the cells post-treatment.

The inventor first measured the cytotoxicity of sorafenib-PLGA microsphere (S20PA52—30 day release formulation) using the following procedures. Colon cancer cells (C26) were seeded in 96 well microtiter plates ($5\times10^3$ cells/well) in 1 mL of RPMI (Rosewell Park Memorial Institute)-1640 medium containing 10% FBS (Fetal Bovine Serum) in a 5% $CO_2$ humidified incubator at 37° C. After 24 h, the cells were treated with 100 μL of six different concentrations of sorafenib-PLGA microsphere solution (2.5, 5, 10, 20, 30 and 40 μg sorafenib/mL). The untreated wells were regarded as a negative control. After 48 h, the medium was removed and 20 μL MTT (5 mg/mL) was added and the resulting solution was incubated for another 4 h at 37° C. Then, the medium was replaced with 150 μL DMSO and the absorbance was measured with a reference wavelength of 630 nm and formazan product absorbance wavelength of 450 nm using a microplate reader (Bio-Tek ELX 800; Bio-Tek Instruments) using a cell proliferation colorimetric assay (MTT based) kit (Sigma-Aldrich, St Louis MO). Each concentration was tested in triplicate. The average absorbance at each concentration for C26 cells is shown in FIG. 5. This study demonstrated that sorafenib was released well from PLGA microsphere into the medium and was relatively potent against C26 cells with demonstrated reduced cell proliferation compared to controls.

In Vivo Study

After completion of the in vitro cytotoxicity study, the inventor performed an in vivo mouse tumor model study using the sorafenib PLGA microsphere (S20PA52). For this study the flank of mice (8 week old female Foxn1nu, The Jackson Laboratory, Bar Harbor ME) were inoculated with C26 cells (2×10⁶ cells) (ATCC, Manassas VA). When the tumor grew to about 200 mm³, the mice were randomized into three groups (6 mice per group) with similar group mean tumor volumes for the following treatments:

Group 1: Sorafenib-PLGA microspheres were injected once using syringe with 21-gauge needle (30 mg sorafenib-PLGA microspheres containing 4.5 mg of sorafenib)

Group 2: Oral sorafenib was given 5 times a week for two weeks (100 mg/kg dose)

Group 3: Solution used in suspending sorafenib-PLGA microspheres was injected as a control ("vehicle").

Tumor length and width were measured over a 2 week period using a digital caliper and tumor volumes were calculated using the formula: Tumor volume=length×width$^2$×0.5236.

Figure 6:
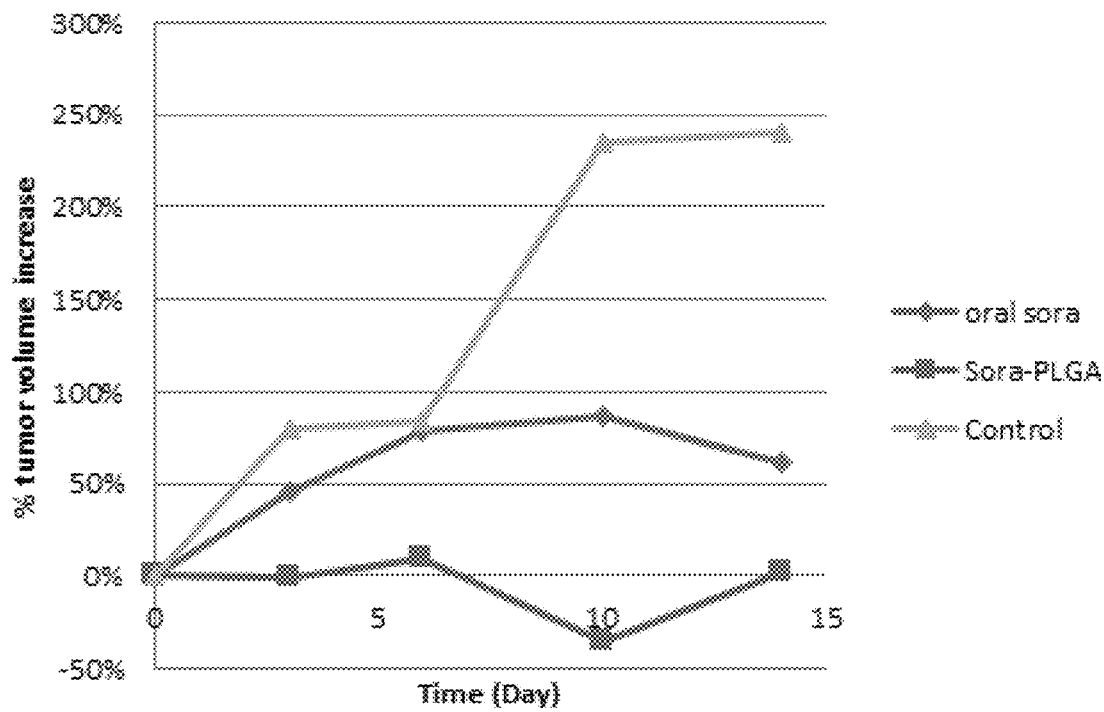
FIG. 6 summarizes the results of an in vivo mouse study showing tumor growth after oral treatment or intratumor injection treatment.

The percentages of tumor growths over 2 weeks for each group, oral versus intratumor injection, are described in FIG. 6. This study demonstrated that intratumor injection of sorafenib-PLGA microsphere was more effective in stopping or slowing down the growth of tumor cells than oral administration of sorafenib. The inventor believes that sorafenib taken orally did not reach, distribute and penetrate well into tumor. In contrast, intratumor injection helped the released sorafenib to distribute and penetrate over whole tumor tissue area.

In addition to the above preliminary mouse model study, the inventor also performed an efficacy comparison between sorafenib-PLGA microsphere (S20PA52) and a combination of sorafenib-PLGA (S20PA52) microsphere and everolimus-PLGA microsphere (E10PA53) [combination-1].

Group 1: Sorafenib-PLGA microspheres were injected once using syringe with 21-gauge needle (30 mg sorafenib-PLGA microspheres containing 4.5 mg of sorafenib)

Group 2: 30 mg of Sorafenib-PLGA microspheres+4 mg of Everolimus-PLGA microspheres (0.6 mg of everolimus)

Group 3: Solution used in suspending sorafenib-PLGA microspheres was injected as a control ("vehicle").

In order to compare the efficacy of both formulations, the tumors were excised at 2 weeks after treatment and their weights were measured. This study demonstrated that the combination-1 with average tumor weight of 0.531 g from 5 mice was more effective in slowing down the growth of tumor than sorafenib alone with that of 0.585 g. The average tumor weight of vehicle control was 0.792 g. The experiment demonstrated that blocking both pathways may reduce the ability of cancer cells to activate other pathways and regrow.

The above studies demonstrated that it was possible to encapsulate both sorafenib and everolimus into PLGA polymers and control their release rate at the cancer site according to the combinatorial targeted cancer treatment method disclosed herein.

The inventor recognizes that to achieve sufficient potency of sorafenib against a tumor, an oral dose of 800 mg per day is required for treating cancer patients. This means that the drug potency is relatively low with regard to application of utilizing local administration such as intratumor dosing. In other words, the low potency of sorafenib requires a very large amount of the drug to be injected into tumor to maintain treatment efficacy over inventor's target of 30-90 days, which is not practical. Therefore, sorafenib in combination-1 may be a good candidate drug delivered daily orally while everolimus may be delivered locally. This method would reduce total systemic side effects. There have been a number of clinical trials to develop systemic delivery of the combination-1 (sorafenib plus everolimus). Many of these trials like examples described below failed due to cumulative systemic side effects:

Hainsworth, J Cancer Investigation, 323-329 (2013)—Kidney cancer

Finn, J Hepatology, 1271-1277 (2013); Koeberle, Annals of Oncology, 856-861 (2016)—Liver cancer Grignani, Lancet Oncology, 98-107 (2015)—Osteosarcoma In order to reduce the systemic side effects, follow-on clinical studies had to modify their dosing schemes by reducing doses or by using intermittent dosing schedules instead of a continuous dosing schedule. However, these modified dosing schemes compromise the efficacy of the combination. So far there has been no systemic combination of sorafenib and everolimus (combination-1) demonstrating successful clinical efficacy in advanced clinical trials, partly due to systemic side effects. The inventor believes that the above clinical failures associated with systemic administration of combination-1 and other combinations can be avoided by the combinatorial targeted therapy described herein.

In Vitro and In Vivo Study for a Combination of Everolimus (mTOR Inhibitor in PI3K Pathway) and Trametinib (MEK Inhibitor in MAPK Pathway)

Considering the issue related to combination-1, the inventor decided to develop a combination of everolimus and trametinib to demonstrate further the usefulness of combinatorial targeted therapy. Both drugs are highly potent requiring less than 10 mg per day orally for treating cancer patients. In addition, it is known from the published clinical literature that when these two potent drugs are combined and taken orally, the combination causes serious systemic side effects. Indeed, two early clinical trials using the same combination described below failed. Tolcher et al. (Annals of Oncol, 58-64 (2015)) investigated the safety and maximum tolerated dose (MTD) of oral trametinib (MEK inhibitor) in combination with oral everolimus (mTOR inhibitor) for 67 patients with advanced solid tumors. This Phase 1 combination treatment study resulted in frequent treatment-related serious side effects. This study was not able to establish a recommended Phase 2 dose and schedule due to severe systemic side effects. Recently, Nikanjam et al. (J. Hematol Oncol Pharm, 19-25 (2023)) concluded that based on the outcome of retrospective clinical data analysis of their cancer patients, they could not support the use of combination of everolimus and trametinib due to serious systemic side effects. In addition, there have been many other attempts to combine inhibitors of both the MAPK and PI3K pathways and perform early clinical trials using systemic administration. Blocking both MAPK and PI3K pathway was termed "horizontal inhibition" by Tolcher (Molecular Cancer Therapeutics, 3-16 (2018)). In contrast, blocking two family proteins in the same MAPK pathway was termed "vertical inhibition" and was somewhat successful. There were three vertical inhibition products approved by the FDA. These are combinations of:

Dabrafenib (RAF inhibitor)+Trametinib (MEK inhibitor)

Encorafenib (RAF inhibitor)+Binimetinib (MEK inhibitor)

Vemurafenib (RAF inhibitor)+Cobimetinib (MEK inhibitor)

These combinations are blocking RAF and MEK in the same MAPK pathway for treating melanoma patients. As far as the inventor is aware, thus far all attempts related to the horizontal inhibition of both MAPK and PI3K pathway have failed during early clinical trials mainly due to cumulative systemic side effects.

For evaluating combination-2, the inventor developed a modified atrigel (in situ gelling=ISG) PLGA formulation instead of PLGA microsphere formulation. A typical atrigel formulation consists of PLGA, drug and N-methyl-2-pyrrolidone (NMP, a biocompatible organic solvent). A solution form of atrigel formulation can be injected into tumor. Upon injection, it becomes a gel immediately forming a drug and PLGA depot. The ISG PLGA formulation is simpler to develop and scale-up for production than PLGA microsphere formulation. The inventor also found that ethanol could be added into the ISG formulation. PLGA is known to be insoluble in ethanol. Therefore, the amount of ethanol should be carefully added into the ISG formulation. The inventor found that up to about 30-40% of ethanol could be added into the typical ISG formulation without causing precipitation of PLGA. Ethanol itself is cytotoxic by disrupting cancer cell membrane and causing necrosis. Ethanol effect during in vitro cytotoxicity study is clearly shown in FIG. 9-FIG. 12.

The inventor performed the following in vitro and in vivo studies using combination-2. These in vitro and in vivo studies were conducted against cancer cell lines with various KRAS mutations. These cell lines include AGS cells which are derived from a human gastric cancer and known to have a G12D KRAS mutation. Initially, the inventor tested the combination ISG formulation of everolimus and trametinib against AGS cells. Later, the inventor also tested the same combination against other cancer cell lines with G12C and G12V KRAS mutations derived from human lung, colorectal and pancreatic cancers:

Mia PcCa-2 cell line (Pancreatic cancer with G12C KRAS mutation)
NCI H441 cell line (Lung cancer with G12V KAS mutation)
SW403 cell line (Colon cancer with G12V KRAS mutation)

As described previously, developing inhibitors directly against mutated KRAS has been very difficult and unsuccessful until recently. Two inhibitors, sotorasib in 2021 and adagrasib in 2022, were approved by the FDA. However, these inhibitors have some significant shortcoming. KRAS has more than 10 subtype mutations depending on the position of the mutation. The above two inhibitors are only effective against G12C KRAS mutation. These inhibitors are not effective against other KRAS subtype mutations such as G12D, G12V and others. The inventor found two published papers describing the successful inhibitions of mutated KRAS with various subtypes during in vitro and in vivo studies using the combination of everolimus and trametinib (Liu, Cancer Chemotherapy and Pharmacology, 1079-1087 (2020)) and the combination of torin-1 (mTOR inhibitor) and trametinib (Brown, Cell Reports Medicine, 1, 10013 (2020)). The Brown paper described their concern with potential systemic side effects from a potential future clinical trial. Furthermore, although they had good outcomes during in vitro and in vivo studies, they did not provide or suggest how they plan to reduce the well-known systemic side effects during clinical settings.

Figure 7:
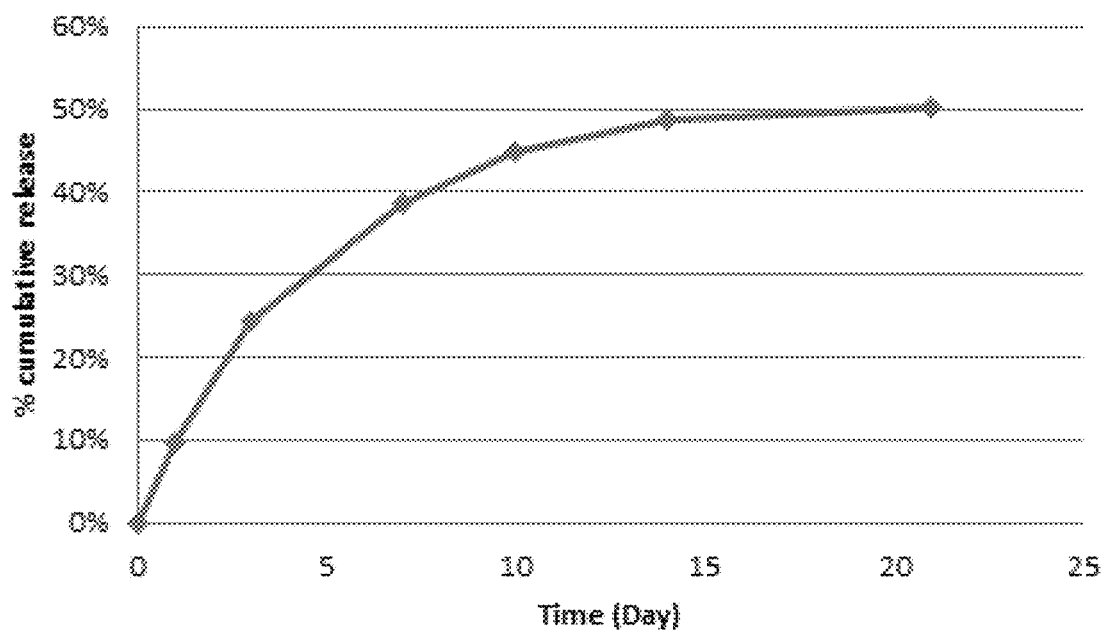
FIGS. 7-8 summarize the results of a study showing percent cumulative release profile of everolimus and trametinib, respectively, in a gel (in situ gelling, ISG) formed from a PLGA solution.

Preparation of ISG Formulation of Everolimus and Trametinib
Everolimus-ISG Formulation:

Place100 mg of PLGA (RG502H by Evonik) in 2 mL of glass vial and add a solution of 300 µL of N-methyl-2-pyrrolidone (NMP) and 100 µL of 100% ethanol into the vial. The resulting mixture was vortexed until PLGA dissolved completely. Then, 15 mg of everolimus (SelleckChem) was added into the solution and the mixture was vortexed until everolimus was completely dissolved. Next, 250 µL of the resulting solution was taken by a syringe and injected into 40 mL of medium (PBS with 0.5% Tween 20) in 50 mL tube. The PLGA solution became a gel immediately upon injection. The tube was incubated 37° C. and at day 1, 3, 7, 10, 14 and 21, the concentrations of everolimus were measured by a HPLC method. Percent (%) cumulative release profile is described in FIG. 7.

Figure 8:
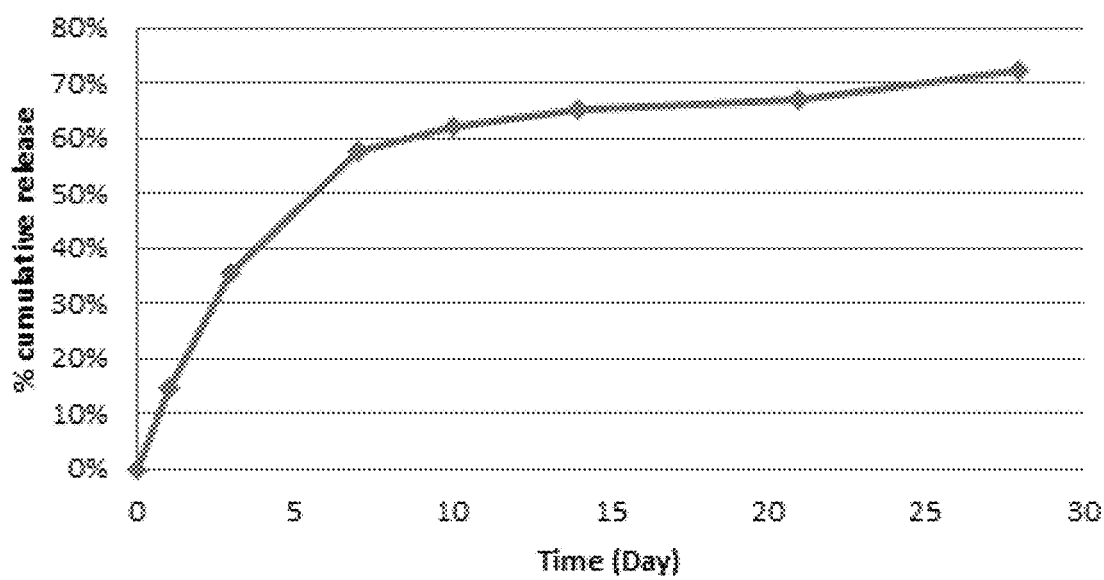
Figure 9:
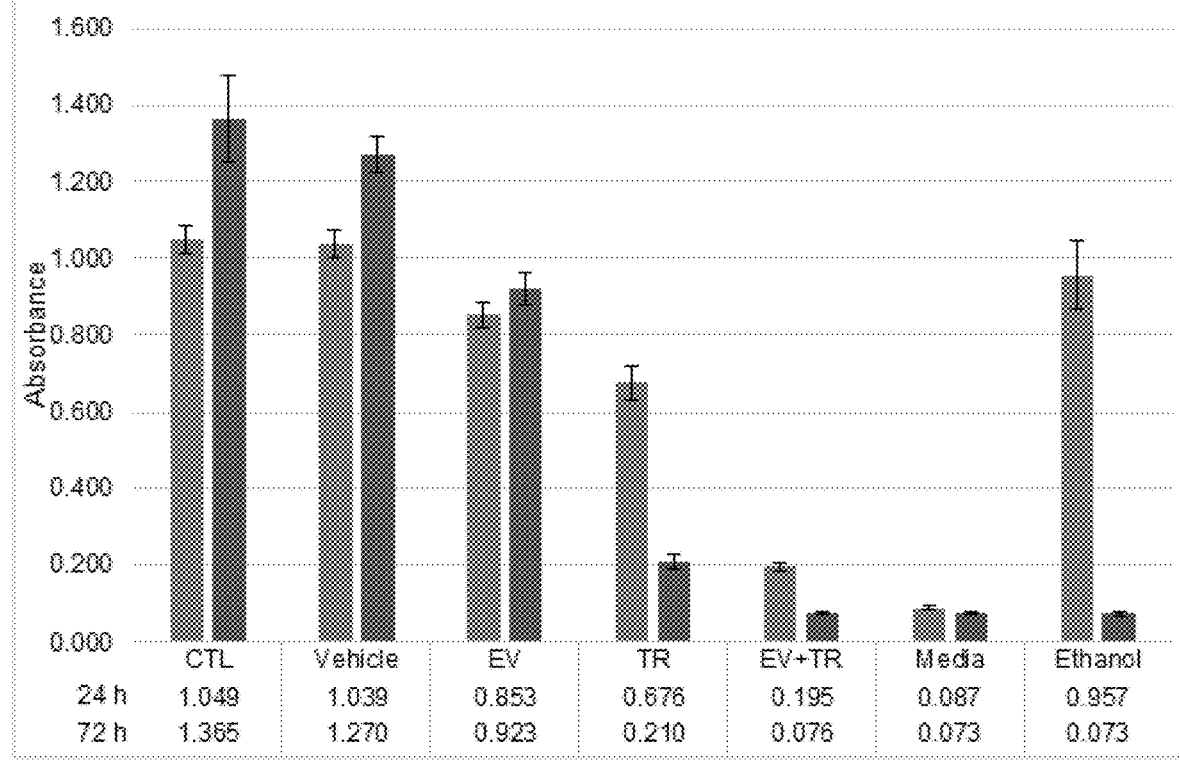
FIGS. 9-12 summarize the results of cell proliferation assay studies using AGS gastric, MIA PaCa-2 pancreatic, NCI H441 lung, and SW403 colorectal cell lines.
Figure 10:
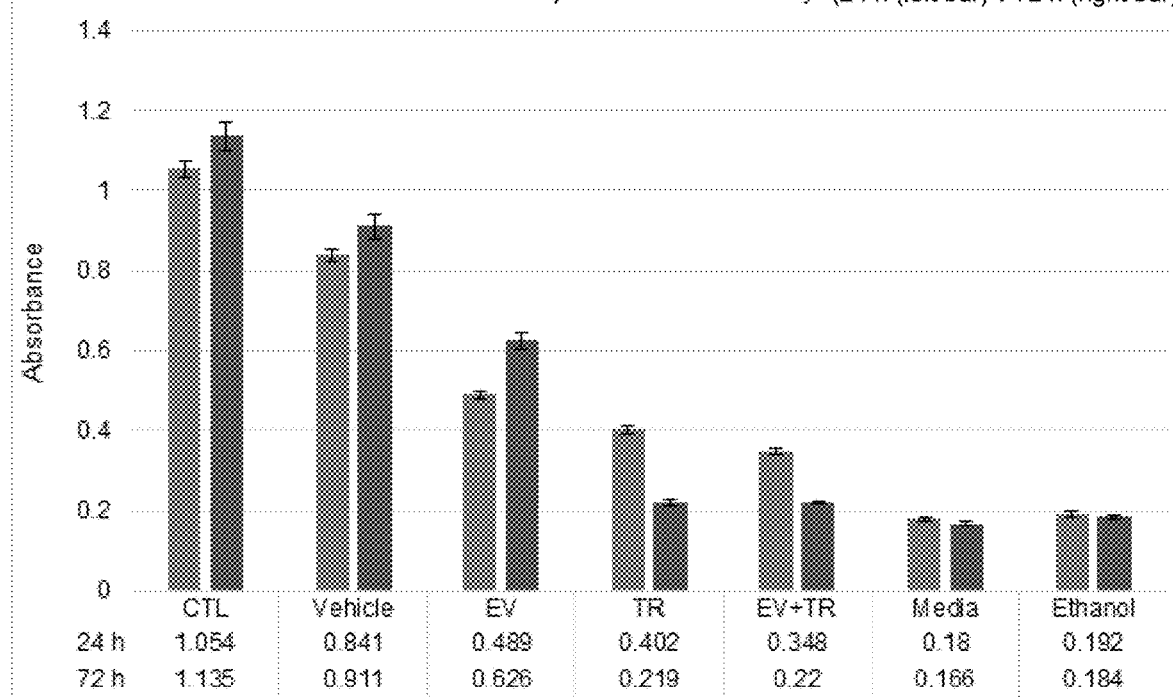
Figure 11:
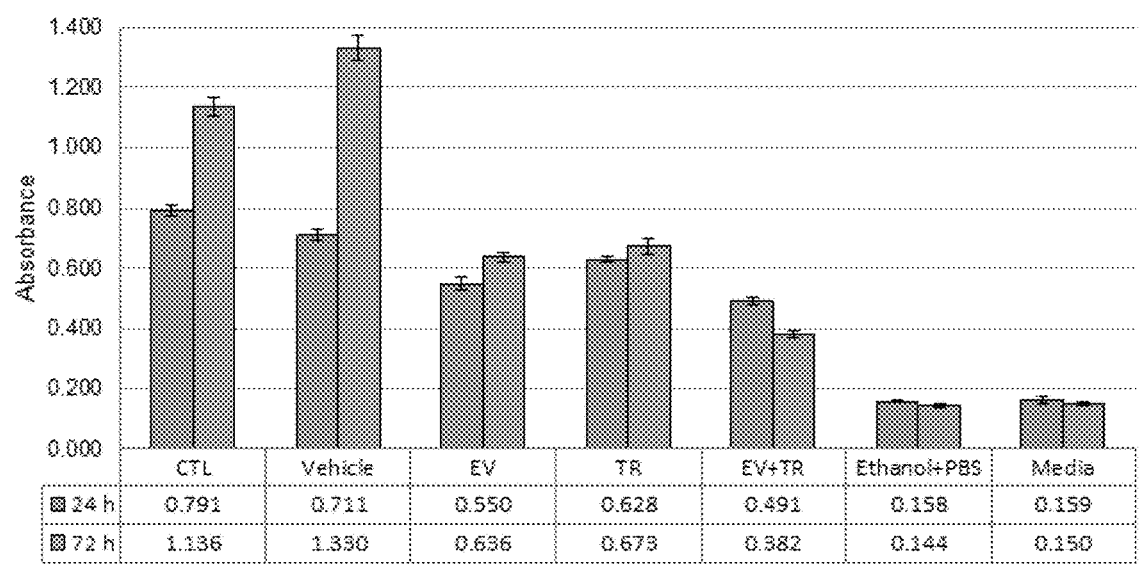
Figure 12:
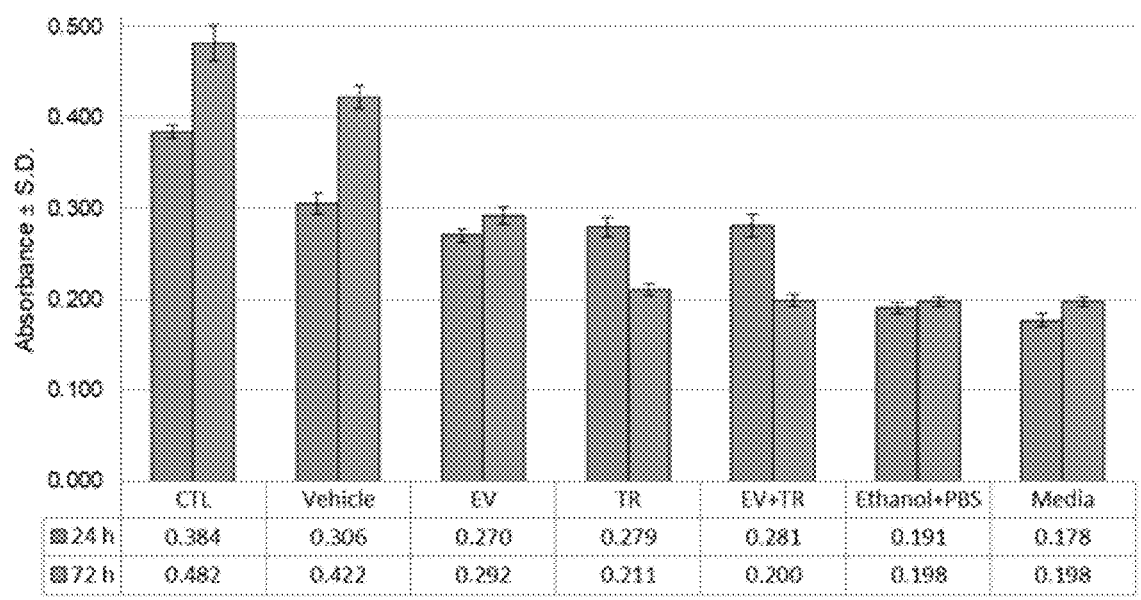

Trametinib-ISG Formulation:

The same preparation procedure described above was used for preparing trametinib formulation except for the addition of 30 mg of PEG (mw=3,350 daltons). In addition, 2% SDS PBS solution instead of 0.5% Tween 20 PBS solution was used for a release medium. Percent (%) cumulative release profile is described in FIG. 8.

HPLC Condition:
Column=Poroshell c18 column (150 mm×4.6 mm×2.7 µm by Agilent)
Mobile phase=0.1% TFA in water: 0.1% TFA in MeOH (17:83)
Retention time: Trametinib=3.1 minutes and Everolimus=6.5 minutes In Vitro Cytotoxicity Study Against AGS Cells AGS cells ($2\times10^4$ cells/well) were seeded in a 12-well plates (Corning, Millipore Sigma) with 1 mL of RPMI-1640 medium containing 10% FBS (Fetal Bovine Serum) and incubated for 1 day at 37° C. in a humidified incubator containing 5% $CO_2$. AGS cells were allowed to proliferate for tests of in vitro antitumor activity. In triplicate wells, Group 1 (PBS), Group 2 (ISG formulation without everolimus or trametinib), Group 3 (ISG formulation with 90 µg of everolimus), Group 4 (ISG formulation with 90 µg of trametinib) and Group 5 (ISG formulation with 90 µg of everolimus and 90 µg of tramethinib), Group 6 (cell culture media without AGS cells) and Group 7 (10% ethanol in cell culture media) were added directly into chambers of the 12 well plate to examine the in vitro antitumor activity of these solutions against AGS cancer cells.

Each 12 well plate chamber was seeded with AGS cells ($2\times10^4$ cells/well). The 12 well plates were maintained at 37° C. in a humidified incubator containing 5% $CO_2$ for 48 hours prior to dosing. To create a drug depot at dosing time, 2 µL of each of the ISG everolimus formulation (90 µg everolimus/well), the ISG trametinib formulation (90 µg trametinib/well) and ISG everolimus-trametinib (90 µg everolimus+90 µg trametinib) formulations were added directly into the media of each corresponding plate well and maintained at 37° C. in a humidified incubator for the duration of the experiment. After 24 and 72 h of ISG exposure, the in vitro cytotoxicity of all formulations against AGS cancer cells was compared using the XTT (methoxynitrosulfophenyl-tetrazolium carboxanilide) assay.

Briefly, 100 µL of PBS solution containing the XTT substrate (50 mg/mL) was added to each 12-well plate and the plates were incubated at 37° C. for 4 h. The resulting formazan precipitate was solubilized by the addition of 500 µL DMSO and shaken for 30 min. The solution of each well was transferred to a 96-well plate (triplicate for wells 1 and 2 and duplicate for well 3) and read using a microplate reader (Bio-teck XLS800; Bio-Tek Instruments City of Industry, CA). The optical density of the formazan product of each well was measured at a wavelength of 450 nm and a reference wavelength of 630 nm. All experiments yielded 8 wells for each test group condition and the results were described as mean±standard deviation in FIG. 9. The results demonstrated that the tested combination was more potent than single drug treatments and ethanol treatment alone appeared to cause complete ablation and cytotoxicity of the cancer cells at the 72 h time point and the concentration tested.

The same cytotoxicity studies were performed against the human MIA PaCa-2 pancreatic, NCI H441 lung and SW403 colorectal cell lines (ATCC, Manassas, VA). The outcomes for the cytotoxicity studies using AGS gastric, MIA PaCa-2 pancreatic, NCI H441 lung, and SW403 colorectal cell lines are described in FIGS. 9, 10, 11, and 12, respectively. As shown in these studies, the cytotoxicity of the combination is higher than that of either everolimus or trametinib alone, showing some synergistic effect. In addition, these 4 cytotoxicity studies confirmed that ethanol appeared to cause ablation with a complete cytotoxic effect on the cancer cells.

In Vivo Mouse Model Study

After the above in vitro cytotoxicity studies, the inventor performed mouse tumor model studies using the ISG-everolimus and ISG-trametinib formulations. These studies were comprised of four groups described below:

Group 1; ISG formulation without drugs and PEG (45 µL)
Group 2: ISG-everolimus formulation (45 µL)
Group 3: ISG-trametinib formulation (45 µL)
Group 4: ISG-everolimus formulation (45 µL)+ISG-trametinib formulation (45 µL)

Ingredients and their amounts in ISG-everolimus and ISG-trametinib formulations are described in Table 1 below:

TABLE 1

| Drug | API | PLGA (502H) Resomer | NMP | EtOH (100%) | PEG (mw = 3,350) | Total |
|---|---|---|---|---|---|---|
| Trametinib | 2 mg | 10 mg | 30 µL | 10 µL | 3 mg | 45 µL |
| Everolimus | 2 mg | 10 mg | 30 µL | 10 µL | — | 45 µL |

Figure 13:
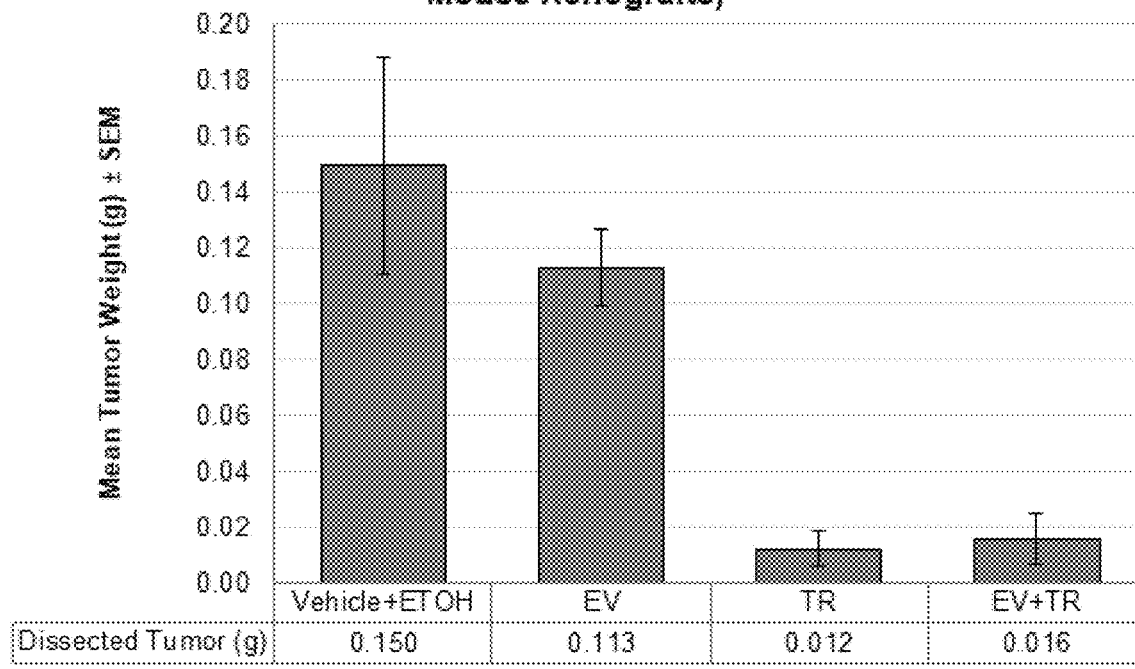
FIG. 13 summarizes the results of mouse tumor model studies with Mia PaCa-2 human pancreatic cancer cell line using the ISG-everolimus and ISG-trametinib formulations.
Figure 14:
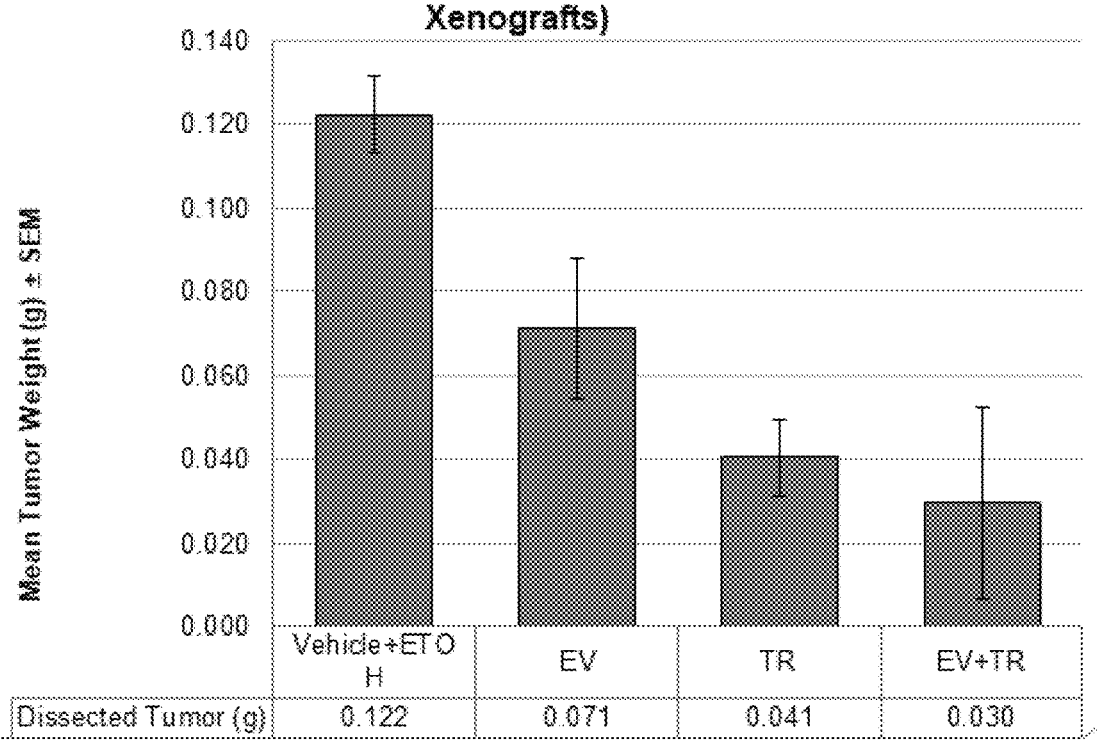
FIGS. 14-15 summarize the results of mouse xenograft studies using NCI H441 human lung cancer and AGS human gastric cancer cell lines, respectively.
Figure 15:
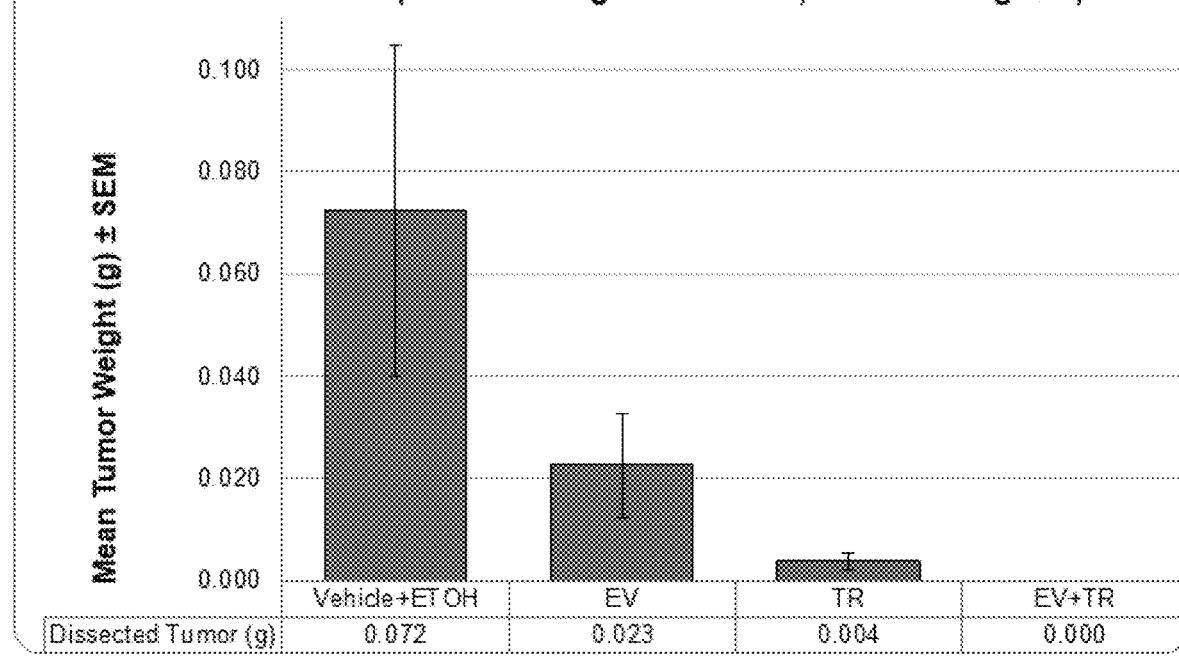
Figure 16A:
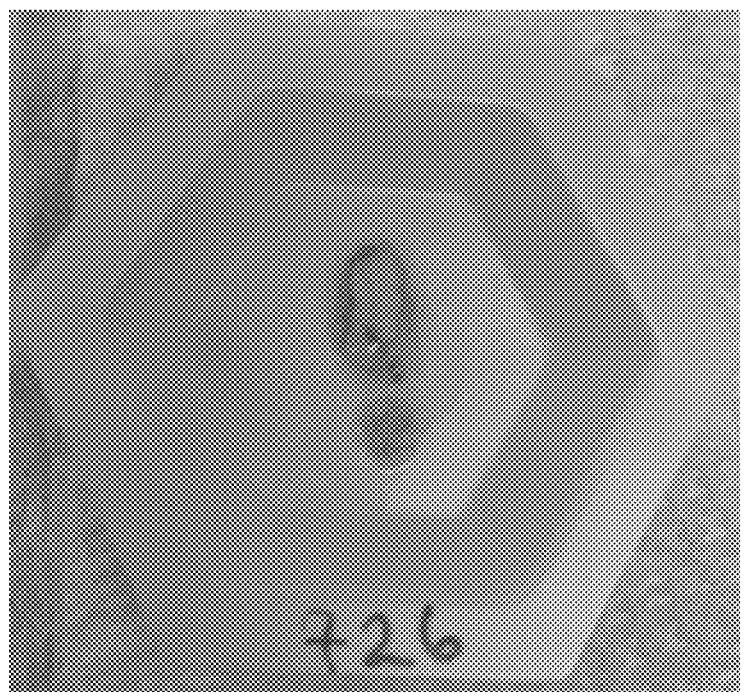
FIGS. 16A-16B depict the excision of gel (FIG. 16A) from an excised tumor (FIG. 16B).
Figure 16B:
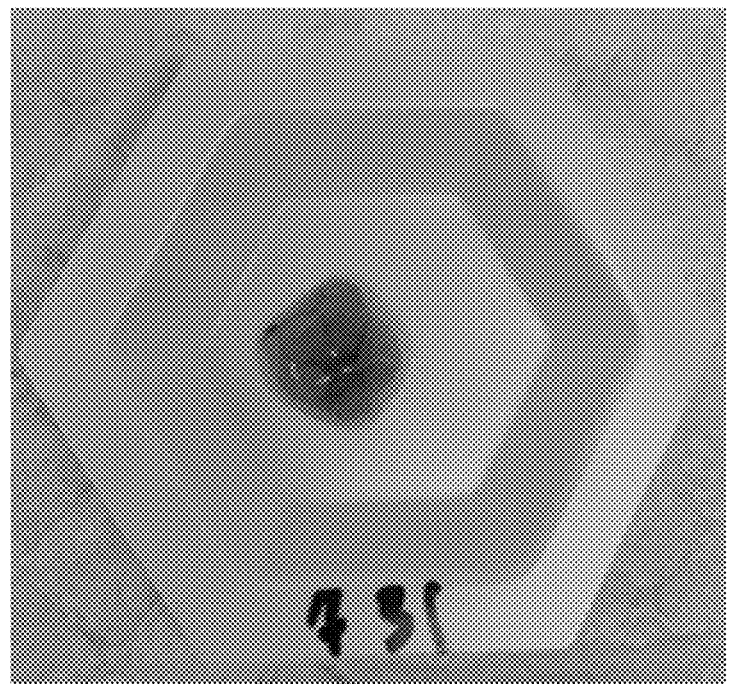

6-8 weeks old Foxnlnu, athymic nude mice (The Jackson Laboratory, Bar Harbor ME) were used for mouse studies. $1\times10^6$ Mia PaCa-2 cells were suspended in 100 µL of Matrigel (Corning) and PBS 1:1 mixture and subcutaneously injected into the flank of each mouse. When tumor volume reached approximately between 50-100 mm$^3$, the mice were divided into different drug treatment groups (n=5 each) to achieve as similar tumor volume means as possible. Mice were dosed with a bolus intratumor injection of the corresponding test group formulation as described above using a Hamilton 100 µL syringe with 20 gauge needle. After one week of treatment, the tumors were excised and weights were measured. The outcome of this experiment is described in FIG. 13. The inventor also performed experiments with the human lung and gastric tumor cells lines NCI H441 and AGS (ATCC, Manassas VA). The outcomes of these studies are described in FIG. 14 and FIG. 15, respectively. Initially the inventor planned to measure the volume of tumor over 3 weeks. However, the inventor found that the gel solidified within the tumor interfered with accurate measurement of the tumor volume by external caliper measurement. Then, the inventor decided to excise the tumor and measure the weight of the tumor after 1 week. When the tumor was excised, the inventor was able to distinguish the gel from the tumor (as shown in FIGS. 16A-16B) to separate out the gel from the excised tumor. The white hard material was identified as the gel (shown in FIG. 16A) and the red soft material was identified as the tumor (shown in FIG. 16B). The weights of the dissected tumors were measured and means, standard deviation and standard error of the means for each group were calculated and compared between groups.

These studies clearly demonstrated that the combination-2 was effective against all three human cancer types (pancreatic, lung and gastric cancer) associated with three major KRAS subtype mutations (G12C, G12D and G12V). Since the combinatorial targeted therapy is blocking downstream family protein of mutated KRAS, i.e. RAF (sorafenib) or MEK (trametinib), the inventor believes that both combination-1 and combination-2 will be effective against other KRAS subtype mutations. This conclusion is supported by the Brown paper (Cell Reports Medicine, 1, 10013 (2020)). Their combination of trametinib and torin-1 (mTOR inhibitor) was active against KRAS G12R subtype mutation along with G12C, G12D and G12V In addition, the inventor intends to apply the combinatorial targeted therapy method to additional combination targeted therapies in pathways other than MAPK and PI3K pathways.

It may be advantageous to set forth definitions of certain words and phrases used in this patent document.

The term "combinatorial targeted therapy" refers to the simultaneous delivery at various cancer sites of multiple targeted drugs through both systemic and local means. The term "combination targeted therapy" refers only to the delivery of multiple targeted drugs.

The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/ or examples. Hence, the scope of the invention is defined by the accompanying claims and their equivalents. Further, each and every claim is incorporated as further disclosure into the specification.

What is claimed is:

1. A combinatorial targeted therapy method for treating a subject having cancer caused by genomic alterations in a PI3K pathway or a MAPK pathway, the method comprising:
   1) performing initial molecular diagnostics to detect the genomic alterations at at least one cancer site of the subject;
   2) for the at least one cancer site, designing an initial combination targeted therapy by selecting a plurality of targeted drugs, based on the results of the initial molecular diagnostic at the at least one cancer site, wherein the plurality of targeted drugs comprises in situ gel for intratumor injection, wherein the in situ gel comprises PLGA formulations, wherein the PLGA formulations comprise PLGA having a molecular weight of 7,000-17,000 daltons and a ratio of PLA: PGA=50:50 in a solution of N-methyl-2-pyrrolidone and ethanol, and having 3.75% to 4.4% w/v of everolimus for inhibiting the PI3K pathway or 3.75% to 4.4% w/v of trametinib for inhibiting the MAPK pathway;
   3) assigning each targeted drug of the plurality of targeted drugs to a systemic delivery method or a local delivery method, based on each targeted drug's properties;
   4) treating the at least one cancer site according to the designed initial combination targeted therapy for the at least one cancer site by delivering each targeted drug according to the assigned delivery method of each targeted drug; wherein the everolimus is released over 1-21 days or the trametinib is released over 1-29 days;
   5) monitoring the progress of the cancer at the at least one cancer site by performing follow-up molecular diagnostics at the at least one cancer site; and
   6) for the at least one cancer site, maintaining the initial combination targeted therapy or designing a follow-up combination targeted therapy, based on the results of the follow-up molecular diagnostics at the at least one cancer site.

2. The method of claim 1 wherein the systemic delivery comprises oral and IV drug delivery.

3. The method of claim 1 wherein properties of the plurality of targeted drugs include known systemic toxicity and potency of the plurality of targeted drugs.

4. The method of claim 3, wherein each drug of the plurality of targeted drugs requiring less than 500 mg oral daily dose is assigned to local delivery.

5. The method of claim 1 wherein the assigning of each targeted drug to systemic or local delivery is further based on the location of the at least one cancer site.

6. The method of claim 1 wherein each targeted drug that is assigned to local delivery is encapsulated in a biodegradable polymer for sustained and controlled release of the targeted drug at the at least one cancer site.

7. The method of claim 6, wherein the biodegradable polymer is PLGA.

8. A combinatorial targeted therapy method for treating a subject having metastatic cancer caused by genomic alterations in a PI3K pathway or a MAPK pathway, the method comprising preventing an unacceptable level of systemic toxicity in the subject by:
   1) performing initial molecular diagnostics to detect the genomic alterations at at least one cancer site of the subject;
   2) for the at least one cancer site, designing an initial combination targeted therapy by selecting a plurality of targeted drugs based on the results of the initial molecular diagnostic at for the at least one cancer site, wherein the plurality of targeted drugs comprises in situ gel for intratumor injection, wherein the in situ gel comprises PLGA formulations having 3.75% to 4.4% w/v of everolimus for inhibiting the PI3K pathway or 3.75% to 4.4% w/v of trametinib for inhibiting the MAPK pathway, in a solution of N-methyl-2-pyrrolidone and ethanol;
   3) assigning each targeted drug of the plurality of targeted drugs to a systemic delivery method or a local delivery method, based on each targeted drug's properties;
   4) treating the at least one cancer site according to the designed initial combination targeted therapy for each site, by delivering each targeted drug according to assigned delivery method to each targeted drug; and
   5) monitoring the progress of the cancer at the at least one cancer site by performing follow-up molecular diagnostics at the at least one cancer site.

9. The method of claim 8 wherein properties of the plurality of targeted drugs include known systemic toxicity and potency of the plurality of targeted drugs.

10. The method of claim 8 wherein the assigning of each targeted drug to systemic or local delivery is further based on the location of the at least one cancer site.

11. The method of claim 8, wherein each drug of the plurality of targeted drugs requiring less than 500 mg oral daily dose is assigned to local delivery.

* * * * *